(12) United States Patent
Fathi et al.

(10) Patent No.: US 9,974,800 B2
(45) Date of Patent: May 22, 2018

(54) THERAPY FOR INHIBITION OF SINGLE-STRANDED RNA VIRUS REPLICATION

(71) Applicant: RedHill Biopharma Ltd., Tel-Aviv (IL)

(72) Inventors: Reza Fathi, Oradell, NJ (US); Dror Ben-Asher, Tel-Aviv (IL); Guy Goldberg, Tel-Aviv (IL)

(73) Assignee: RedHill Biopharma Ltd., Tel-Aviv (IL)

( * ) Notice: Subject to any disclaimer, the term of this patent is extended or adjusted under 35 U.S.C. 154(b) by 0 days. days.

(21) Appl. No.: 14/921,661

(22) Filed: Oct. 23, 2015

(65) Prior Publication Data

US 2016/0113954 A1    Apr. 28, 2016

Related U.S. Application Data

(60) Provisional application No. 62/068,465, filed on Oct. 24, 2014, provisional application No. 62/068,469, filed on Oct. 24, 2014, provisional application No. 62/068,477, filed on Oct. 24, 2014, provisional application No. 62/068,487, filed on Oct. 24, 2014, provisional application No. 62/068,492, filed on Oct. 24, 2014, provisional application No. 62/188,030, filed on Jul. 2, 2015.

(51) Int. Cl.
*A61K 31/7048* (2006.01)
*A61K 31/435* (2006.01)
*A61K 31/4409* (2006.01)
*A61K 45/06* (2006.01)
*A61K 31/438* (2006.01)

(52) U.S. Cl.
CPC ........ *A61K 31/7048* (2013.01); *A61K 31/435* (2013.01); *A61K 31/438* (2013.01); *A61K 31/4409* (2013.01); *A61K 45/06* (2013.01)

(58) Field of Classification Search
CPC .............. A61K 31/435; A61K 31/4409; A61K 31/7048; A61K 45/06; A61K 31/438; A61K 2300/00
USPC .................................................. 514/29, 357
See application file for complete search history.

(56) References Cited

U.S. PATENT DOCUMENTS

| 2003/0045746 A1 | 3/2003 | Jomaa |
| 2004/0131604 A1 | 7/2004 | Clark |
| 2012/0095004 A1 | 4/2012 | Smith et al. |
| 2013/0230860 A1 | 9/2013 | Park et al. |

OTHER PUBLICATIONS

Inoue et al. Open label trial of clarithromycin therapy in Japanese patients with Crohn's disease. Journal of Gastroenterology and Hepatology 22 (2007) 984-988.*
Geisbert et al. Pathogenesis of Ebola Hemorrhagic Fever in Cynomolgus Macaques. Am J Pathol 2003, 163:2347-2370.*
Madrid et al. A Systematic Screen of FDA-Approved Drugs for Inhibitors of Biological Threat Agents. PLoS One 8(4): e60579, Published Apr. 5, 2013.*
Veljkovic et al. Virtual screen for repurposing approved and experimental drugs for candidate inhibitors of Ebola virus infection. F1000Research 2015, 4:34 Last updated: Feb. 12, 2015. (Year: 2015).*
International Search Report and Written Opinion from International Appln. No. PCT/IB2015/002173 dated Mar. 21, 2016.
Krishnan et al., "Effects of interactions of antibacterial drugs with each other and with 6-mercaptopurine on in vitro growth of *Mycobacterium avium* subspecies paratuberculosis", Journal of Antimicrobial Chemotherapy, 2009, 64 pp. 1018-1023.

* cited by examiner

*Primary Examiner* — Yih-Horng Shiao
(74) *Attorney, Agent, or Firm* — Greenberg Traurig, LLP

(57) ABSTRACT

Pharmaceutical compositions showing the ability to inhibit or suppress replication of a filovirus in an individual are disclosed. The disclosed compositions are useful for treating, reventing, or reducing the spread of infections by filovirus. A method includes administering at least one agent of the present disclosure to an individual infected with or exposed to a filovirus, wherein the step of administering is carried out for a suitable time period so that the individual is treated; and determining whether the individual has been treated, wherein the step of determining includes one of measuring an inhibition in viral replication, measuring a decrease in viral load, or reducing at least one symptom associated with the filovirus.

8 Claims, No Drawings

THERAPY FOR INHIBITION OF SINGLE-STRANDED RNA VIRUS REPLICATION

RELATED APPLICATIONS

This application claims the benefit of and priority to U.S. Provisional Patent Application No. 62/068,465, filed Oct. 24, 2014, U.S. Provisional Patent Application No. 62/068,469, filed Oct. 24, 2014, U.S. Provisional Patent Application No. 62/068,477, filed Oct. 24, 2014, U.S. Provisional Patent Application No. 62/068,487, filed Oct. 24, 2014, U.S. Provisional Patent Application No. 62/068,492, filed Oct. 24, 2014, and U.S. Provisional Patent Application No. 62/188,030, filed Jul. 2, 2015, the entirety of these applications is hereby incorporated herein by reference.

BACKGROUND

RNA viruses can be classified according to the sense or polarity of their RNA into negative-sense (−) and positive-sense (+) RNA viruses. The largest family of viruses is the single stranded negative-sense (−) RNA ("ssRNA") family of viruses. Their viral RNA genome cannot be directly translated, instead the (−) strand is complementary to the viral mRNAs that need to be produced and translated into viral proteins. At the time of this disclosure, one order and eight families are recognized in this group. There are also a number of unassigned species and genera:

Order Mononegavirales
Family Bornaviridae—Borna disease virus
Family Filoviridae—includes Ebola virus, Marburg virus
Family Paramyxoviridae—includes Measles virus, Mumps virus, Nipah virus, Hendra virus, RespiratorySyncytial Virus (RSV), and Newcastle Disease Virus (NDV)
Family Rhabdoviridae—includes Rabies virus
Family Nyamiviridae—includes Nyavirus
Unassigned families:
Family Arenaviridae—includes Lassa virus
Family Bunyaviridae—includes Hantavirus, Crimean-Congo hemorrhagic fever
Family Ophioviridae
Family Orthomyxoviridae—includes Influenza viruses
Unassigned genera:
Genus Deltavirus—includes Hepatitis D virus
Genus Dichorhavirus
Genus Emaravirus
Genus Nyavirus—includes Nyamanini and Midway viruses
Genus Tenuivirus
Genus Varicosavirus
Unassigned species:
Taastrup virus
*Sclerotinia sclerotiorum* negative-stranded RNA virus 1

Despite decades of efforts by researchers to develop an effective, approved, and available filovirus treatment for individuals, currently there are no United States Food and Drug Administration-approved vaccines or therapeutics for treatment of infection with filovirus diseases.

SUMMARY

Therapies for the inhibition of single-stranded RNA virus replication are disclosed herein. Compositions and methods for treating symptomatic and/or asymptomatic infections of negative-sense single-stranded RNA viruses including, but not limited to, Bornaviridae, Filoviridae, Paramyxoviridae, Rhabdoviridae, Nyamiviridae or any combination thereof, are disclosed herein. In an embodiment, therapy for inhibition of an Ebola virus is disclosed herein. In an embodiment, therapy for inhibition of Marburg virus is disclosed herein.

A method of the present invention includes administering a compound to an individual infected with or exposed to a filovirus, wherein the step of administering is carried out for a suitable time period so that the individual is treated, and wherein the compound is represented by formula I:

(I)

or a pharmaceutically acceptable salt thereof, wherein:
$R_1$ is phenyl, 4-chlorophenyl or 4-fluorophenyl,
$R_2$ is 4-pyridyl, optionally substituted with up to 4 groups that are independently ($C_1$-$C_6$) alkyl, halogen, haloalkyl, —OC(O)($C_1$-$C_6$ alkyl), —C(O)O($C_1$-$C_6$ alkyl), —CONR'R", —OC(O)NR'R", —NR'C(O)R", —$CF_3$, —$OCF_3$, —OH, $C_1$-$C_6$ alkoxy, hydroxyalkyl, —CN, —$CO_2$H, —SH, —S-alkyl, —SOR'R", —$SO_2$R', —$NO_2$, or NR'R", wherein R' and R" are independently H or ($C_1$-$C_6$) alkyl, and wherein each alkyl portion of a substituent is optionally further substituted with 1, 2, or 3 groups independently selected from halogen, CN, OH, and $NH_2$,
$R_4$ is H or alkyl, and
n is 1 or 2; and
determining whether the individual has been treated, wherein the step of determining comprising one of measuring an inhibition in viral replication, measuring a decrease in viral load, or reducing at least one symptom associated with the filovirus. In an embodiment, the compound of formula I is:

3-(4-Chloro-phenyl)-adamantane-1-carboxylic acid (pyridin-4-ylmethyl)-amide

In an embodiment, the compound of formula I is administered at a daily dosage ranging from about 2.5 mg/kg to about 22.5 mg/kg. In an embodiment, the compound of formula I is administered at a daily dosage ranging from about 3.5 mg/kg to about 21.5 mg/kg. In an embodiment, the compound of formula I is administered at a daily dosage ranging from about 4.5 mg/kg to about 20.5 mg/kg. In an embodiment, the compound of formula I is administered at a daily dosage ranging from about 5.5 mg/kg to about 19.5 mg/kg. In an embodiment, the compound of formula I is administered at a daily dosage ranging from about 6.5 mg/kg to about 18.5 mg/kg. In an embodiment, the compound of formula I is administered at a daily dosage ranging from about 7.5 mg/kg to about 17.5 mg/kg. In an embodiment, the compound of formula I is administered at a daily dosage ranging from about 8.5 mg/kg to about 16.5 mg/kg. In an embodiment, the compound of formula I is administered at a daily dosage ranging from about 9.5 mg/kg to about 15.5 mg/kg. In an embodiment, the compound of formula I is administered at a daily dosage ranging from about 10.5 mg/kg to about 14.5 mg/kg. In an embodiment, the compound of formula I is administered at a daily dosage ranging from about 11.5 mg/kg to about 13.5 mg/kg. In an embodiment, the determining step includes measuring, at at least two different times during the suitable time period, the viral load using a nucleic acid amplification based test. In an embodiment, the inhibition in viral replication or the decrease in viral load is at least 10% as determined using a nucleic acid amplification based test. In an embodiment, the individual is a human. In an embodiment, the filovirus is Ebola virus or Marburg virus. In an embodiment, the filovirus is Ebola virus. In an embodiment, the compound of formula I is present as a solid dosage form. In an embodiment, the solid dosage form is a capsule. In an embodiment, the method further includes administering at least one antibiotic to the individual infected with or exposed to the filovirus for the suitable time period, wherein the combination of the at least one antibiotic and the compound of formula I produce a synergistic effect. In an embodiment, the at least one antibiotic is selected from one of clarithromycin or rifabutin.

A method of the present invention includes administering at least two antibiotics to an individual infected with or exposed to a filovirus, wherein the step of administering is carried out for a suitable time period so that the individual is treated; and determining whether the individual has been treated, wherein the step of determining includes one of measuring an inhibition in viral replication, measuring a decrease in viral load, or reducing at least one symptom associated with the filovirus. In an embodiment, at least one of the antibiotics is a macrolide antibiotic. In an embodiment, at least one of the antibiotics is a rifamycin antibiotic. In an embodiment, the antibiotics are clarithromycin and rifabutin. In an embodiment, clarithromycin is administered at a daily dosage ranging from about 2.5 mg/kg to about 21.5 mg/kg. In an embodiment, clarithromycin is administered at a daily dosage ranging from about 3.5 mg/kg to about 20.5 mg/kg. In an embodiment, clarithromycin is administered at a daily dosage ranging from about 4.5 mg/kg to about 19.5 mg/kg. In an embodiment, clarithromycin is administered at a daily dosage ranging from about 5.5 mg/kg to about 18.5 mg/kg. In an embodiment, clarithromycin is administered at a daily dosage ranging from about 6.5 mg/kg to about 17.5 mg/kg. In an embodiment, rifabutin is administered at a daily dosage ranging from about 7.5 mg/kg to about 16.5 mg/kg. In an embodiment, clarithromycin is administered at a daily dosage ranging from about 8.5 mg/kg to about 15.5 mg/kg. In an embodiment, clarithromycin is administered at a daily dosage ranging from about 9.5 mg/kg to about 14.5 mg/kg. In an embodiment, rifabutin is administered at a daily dosage ranging from about 10.5 mg/kg to about 13.5 mg/kg. In an embodiment, rifabutin is administered at a daily dosage ranging from about 0.5 mg/kg to about 7.5 mg/kg. In an embodiment, rifabutin is administered at a daily dosage ranging from about 1.5 mg/kg to about 6.5 mg/kg. In an embodiment, rifabutin is administered at a daily dosage ranging from about 2.5 mg/kg to about 5.5 mg/kg. In an embodiment, the determining step includes measuring, at at least two different times during the suitable time period, the viral load using a nucleic acid amplification based test. In an embodiment, the inhibition in viral replication or the decrease in viral load is at least 10% as determined using a suitable assay. In an embodiment, the individual is a human. In an embodiment, the filovirus is Ebola virus or Marburg virus. In an embodiment, the filovirus is Ebola virus.

DETAILED DESCRIPTION

As used herein, the term "agent" refers to a compound having a pharmacological activity—an effect of the agent on an individual. The terms "agent," "compound," and "drug" are used interchangeably herein.

A "patient" or an "individual" refers to any animal, such as a primate. In an embodiment, the primate is a non-human primate. In an embodiment, the primate is a human primate. Any animal can be treated using the methods and composition of the present invention.

As used herein, the term "synergistic effect" refers to the coordinated or correlated action of two or more agents of the present invention so that the combined action is greater than the sum of each acting separately. In an embodiment, agents of the present invention, when administered together as part of a treatment regimen, provide a therapeutic synergy without accompanying synergistic side effects (e.g., but not limited to, cross-reacting agents).

As used herein, the term "treat" is meant to administer one or more agents of the present invention to measurably inhibit the replication of a virus in vitro or in vivo, to measurably decrease the load of a virus in a cell in vitro or in vivo, or to reduce at least one symptom associated with having a filovirus-mediated disease in a patient. Desirably, the inhibition in replication or the decrease in viral load is at least 10%, 15%, 20%, 25%, 30%, 35%, 40%, 45%, 50%, 55%, 60%, 65%, 70%, 75%, 80%, 85%, 90%, 95%, 97%, 98%, 99%, as determined using a suitable assay. Assays that monitor replication of viruses include, but are not limited to, cytopathic viral assays, reporter-virus and reporter-cell assays, viral replicon assays, and gene-targeted viral assays. In an embodiment, an assay that measures CD8 T cell-mediated inhibition of filovirus replication is used to measure the slow or stop in the replication of a virus. Viral load testing can be carried out using nucleic acid amplification based tests (NATs or NAATs) and non-nucleic acid-based tests on blood plasma samples to determine the quantity of virus in a given volume including viral RNA levels in plasma and tissue and total viral DNA. Alternatively, in certain embodiments, treatment is observed by a trained physician as an appreciable or substantial relief of symptoms in a patient with a filovirus-mediated disease. Typically, a decrease in viral replication is accomplished by reducing the rate of RNA polymerization, RNA translation, protein processing or modification, or by reducing the activity of a molecule involved in any step of viral replication (e.g., proteins or coded by the genome of the virus or host important for viral replication). In an embodiment, the term "treat" refers to the ability of an agent or agents of the present invention to inhibit or suppress replication of a virus, such as an RNA virus. In an embodiment, the term "treat" refers to the ability of an agent or agents of the present invention to inhibit the cytopathic effect during a RNA virus infection.

By an "effective amount" is meant the amount of an agent or agents of the present invention, alone or in combination with another therapeutic regimen, required to treat a patient with a viral disease (e.g., any virus described herein including an Ebola virus or Marburg virus) in a clinically relevant manner. A sufficient effective amount of an agent or agents used to practice the present invention for therapeutic treatment of conditions caused by a virus varies depending upon the manner of administration, the age, body weight, and general health of the patient. Ultimately, the prescribers will decide the appropriate amount and dosage regimen. In a combination therapy of the invention, the effective amount of an agent may be less than the effective amount if the agent were administered in a non-combinatorial (single-agent) therapy. Additionally, an effective amount may be an amount of an agent in a combination therapy of the invention that is safe and efficacious in the treatment of a patient having a viral disease over each agent alone as determined and approved by a regulatory authority (such as the U.S. Food and Drug Administration).

By "more effective" is meant that a treatment exhibits greater efficacy, or is less toxic, safer, more convenient, or less expensive than another treatment with which it is being compared. Efficacy may be measured by a skilled practitioner using any standard method that is appropriate for a given indication.

By a "filovirus" is meant a virus belonging to the family Fillovirdae. Exemplary filoviruses are Ebola virus and Marburg virus.

"Ebola" or "Ebola hemorrhagic fever" is a disease caused by infection with one of the Ebola virus strains. Ebola can cause disease in humans and nonhuman primates (monkeys, gorillas, and chimpanzees). Ebola disease in humans is caused by four of five viruses in the genus Ebolavirus. The four are Bundibugyo virus (BDBV), Sudan virus (SUDV), Tai Forest virus (TAFV), and one called, simply, Ebola virus (EBOV, formerly Zaire Ebola virus). The fifth virus, Reston virus (RESTV), is not thought to cause disease in humans, but has caused disease in other primates. These five viruses are closely related to marburgviruses. Marburg virus disease (MVD) is a severe illness of humans and non-human primates caused by either of the two marburgviruses, Marburg virus and Ravn virus.

As used herein, the term "a suitable period of time" refers to the period of time starting when a patient begins treatment for a diagnosis of ssRNA viral infection (e.g., but not limited to, Ebola) using a method of the present disclosure, throughout the treatment, and up until when the patient stops treatment due to either a reduction in symptoms associated with ssRNA viral infection (e.g., but not limited to, Ebola) or due to a laboratory diagnosis indicating that the ssRNA viral infection (e.g., but not limited to, Ebola) is under control. In an embodiment, a suitable period of time is one (1) week. In an embodiment, a suitable period of time is between one (1) week and two (2) weeks. In an embodiment, a suitable period of time is two (2) weeks. In an embodiment, a suitable period of time is between two (2) weeks and three (3) weeks. In an embodiment, a suitable period of time is three (3) weeks. In an embodiment, a suitable period of time is between three (3) weeks and four (4) weeks. In an embodiment, a suitable period of time is four (4) weeks. In an embodiment, a suitable period of time is between four (4) weeks and five (5) weeks. In an embodiment, a suitable period of time is five (5) weeks. In an embodiment, a suitable period of time is between five (5) weeks and six (6) weeks. In an embodiment, a suitable period of time is six (6) weeks. In an embodiment, a suitable period of time is between six (6) weeks and seven (7) weeks. In an embodiment, a suitable period of time is seven (7) weeks. In an embodiment, a suitable period of time is between seven (7) weeks and eight (8) weeks. In an embodiment, a suitable period of time is eight (8) weeks.

As used herein, the term "cytopathic effects" refers to the changes in cell morphology due to a viral infection.

As used herein, the terms "cytopathogenesis" or "pathogenesis" includes inhibition of host cell gene expression and includes other cellular changes that contribute to viral pathogenesis in addition to those changes that are visible at the microscopic level.

The term "in vitro" as used herein refers to procedures performed in an artificial environment, such as for example, without limitation, in a test tube or cell culture system. The skilled artisan will understand that, for example, an isolate SK enzyme may be contacted with a modulator in an in vitro environment. Alternatively, an isolated cell may be contacted with a modulator in an in vitro environment.

The term "in vivo" as used herein refers to procedures performed within a living organism such as, without limitation, a human, monkey, mouse, rat, rabbit, bovine, equine, porcine, canine, feline, or primate.

Some small viruses carry their genome as single-stranded DNA (ssDNA) molecules. These viruses have a simple genome: one gene for a viral nucleocapsid protein and another gene for a DNA replication enzyme. The virus with a ssDNA genome also faces a serious replication problem in the host cell. When introduced into cells, these genomes cannot be used to make viral proteins because the only template for transcription is double-stranded DNA. For this reason, the first step after infection is the conversion of the viral ssDNA into dsDNA using host cell DNA polymerase. In some of these viruses, the 3' end of the viral DNA folds back and forms dsDNA by base-pairing with an internal sequence. In this way, the primer is built into the genome and the 3' end can be extended to create dsDNA that serves as a template for transcription. The resulting transcripts are translated to make the viral proteins, the replicated viral DNA is converted back into a ssDNA genome, and the virion is packaged for export.

RNA viruses can be classified according to the sense or polarity of their RNA into negative-sense (−) and positive-sense (+), or ambisense RNA viruses. Positive-sense viral RNA is similar to mRNA and thus can be immediately translated by the host cell. Negative-sense viral RNA is complementary to mRNA and thus must be converted to positive-sense RNA by an RNA polymerase before translation. As such, purified RNA of a positive-sense virus can directly cause infection though it may be less infectious than the whole virus particle. Purified RNA of a negative-sense virus is not infectious by itself as it needs to be transcribed into positive-sense RNA; each virion can be transcribed to several positive-sense RNAs. Ambisense RNA viruses resemble negative-sense RNA viruses, except they also translate genes from the positive strand. Examples of positive-strand RNA viruses include, but are not limited to, polio virus, Coxsackie virus, and echovirus. Examples of negative-strand RNA viruses include, but are not limited to, influenza virus, measles viruses, and rabies virus.

The largest family of viruses is the (−) ssRNA family of viruses. Their viral RNA genome cannot be directly translated, instead the (−) strand is complementary to the viral mRNAs that need to be produced and translated into viral proteins. Nature has created hundreds of different (−) ssRNA viruses ranging from the measles and influenza viruses to the rabies and Ebola viruses. Members of this class of virus include Ebola virus and members of the influenza family of viruses.

Ebola, previously known as Ebola hemorrhagic fever, is a disease caused by infection with one of the Ebola virus strains. Ebola can cause disease in humans and nonhuman primates (monkeys, gorillas, and chimpanzees). Ebola disease in humans is caused by four of five viruses in the genus Ebolavirus. The four are Bundibugyo virus (BDBV), Sudan virus (SUDV), Tai Forest virus (TAFV), and one called, simply, Ebola virus (EBOV, formerly Zaire Ebola virus). The fifth virus, Reston virus (RESTV), is not thought to cause disease in humans, but has caused disease in other primates. These five viruses are closely related to marburgviruses. Currently, no specific therapy is available that has demonstrated efficacy in the treatment of Ebola.

Ebolaviruses contain single-strand, non-infectious RNA genomes. Ebolavirus genomes are approximately 19 kilobase pairs long and contain seven genes in the order 3'-UTR—NP-VP35-VP40-GP-VP30-VP24-L-5'-UTR. The genomes of the five different ebolaviruses (BDBV, EBOV, RESTV, SUDV, and TAFV) differ in sequence and the number and location of gene overlaps. In general, ebolavirions are 80 nanometers (nm) in width and may be as long as 14,000 nm. In general, the median particle length of ebolaviruses ranges from 974 to 1,086 nm (in contrast to marburgvirions, whose median particle length was measured at 795-828 nm), but particles as long as 14,000 nm have been detected in tissue culture.

The viral matrix protein 40 (VP40) is the most abundant protein found in the virions, in infected cells, and also inside the viral nucleocapsid. The nucleoprotein (NP) is associated with the viral genome and assembled into a helical nucleocapside (NC) along with polymerase cofactor (VP35), the transcription activator (VP30), and the RNA-dependent RNA polymerase (L). The viral proteins that comprise the NC catalyze the replication and transcription of the viral genome. A minor viral matrix protein, VP24 is also required for NC assembly. If NP is expressed alone in cells, it assembles together with cellular RNA to form a loose coil-like structure. When NP is co-expressed with VP24 and VP35, NC-like structures are formed in the cytoplasm that are morphologically indistinguishable from those seen in infected cells. It has been shown that VP24 and the viral matrix protein VP40 reduce the transcription and replication efficiencies of the EBOV genome, suggesting that VP24 and VP40 are important for the conversion from a transcription and replication-competent NC to one that is ready for viral assembly. VP40 plays a role in the formation and release of the enveloped, filamentous virus-like particles (VLPs) even when expressed alone. NC-like structures are incorporated into VLPs when VP40 is co-expressed with NP, VP35, and VP24, suggesting that a direct interaction between VP40 and NP is important for the recruitment of NC-like structures to the budding site, the plasma membrane. The interaction between VP40 and NP is also required for the formation of condensed NC-like structures. GP is a surface glycoprotein that forms spikes on virions and plays a crucial role in virus entry into cells by mediating receptor binding and fusion.

The ebolavirus life cycle begins with virion attachment to specific cell-surface receptors, followed by fusion of the virion envelope with cellular membranes and the concomitant release of the virus nucleocapsid into the cytosol. Ebolavirus' structural glycoprotein (known as GP1,2) is responsible for the virus' ability to bind to and infect targeted cells. The viral RNA polymerase, encoded by the L gene, partially uncoats the nucleocapsid and transcribes the genes into positive-strand mRNAs, which are then translated into structural and nonstructural proteins. The most abundant protein produced is the nucleoprotein, whose concentration in the cell determines when L switches from gene transcription to genome replication. Replication results in full-length, positive-strand antigenomes that are, in turn, transcribed into negative-strand virus progeny genome copy. Newly synthesized structural proteins and genomes self-assemble and accumulate near the inside of the cell membrane. Virions bud off from the cell, gaining their envelopes from the cellular membrane they bud from. The mature progeny particles then infect other cells to repeat the cycle. The Ebola virus genetics are difficult to study due to its virulent nature.

Ebola is a filamentous, enveloped, negative-sense RNA strand virus in the family of Filoviridae. The RNA-dependent RNA-polymerase of Ebola virus shares significant sequence homology to other negative-strand RNA viruses, required for both viral transcription and replication of the viral genome. However, RNA-dependent RNA-polymerase requires a host factor and viral proteins cooperating to accomplish replication and transcription. One of the reasons why Ebola is so deadly is due to its ability to circumvent the immune system while at the same time pro-actively destroying the human body, as a result the immune system is not able to gather a cohesive effort to fight off the disease. During the infection, monocytes/macrophages in the lymphoid tissues are early and sustained targets of this deadly virus. During the viral infection, large amounts of proinflammatory cytokines such as tumor necrosis factor (TNF-α) are secreted from infected macrophages and cause disruption of the endothelial barrier. Macrophages and Dendritic cells play a central role in inducing the observed clinical feature of Ebola's hemorrhagic fever. Secreted cytokines, chemokines, and other mediators alter the blood vessel functions, promote and recruit an influx of inflammatory cells, including additional monocytes/macrophages to the site of the infection. The virus released from the infected macrophages and dendritic cells spread to similar cells throughout the body and to parenchymal cells in many organs, resulting in multifocal tissue necrosis. The ability of the host to develop an effective adaptive immune response is weakened by massive lymphocyte apoptosis, a phenomenon also seen in bacterial sepsis. Ebola infection also induces lymphocyte apoptosis, although the virus does not replicate in lymphocytes. Recent studies indicate that NK (Natural Killer) cells and CD4+ and CD8+ lymphocytes are the principal cell types affected in Ebola-infected macaques monkeys.

An Ebola subject who shows symptoms (i.e., is symptomatic) including, but not limited to, high fever, headache, joint and muscle aches, sore throat, weakness, stomach pain, lethargy, and lack of appetite, can undergo blood and/or tissue tests to confirm an Ebola diagnosis. An Ebola subject who does not show symptoms (i.e., is asymptomatic) can undergo blood and/or tissue tests to confirm an Ebola diagnosis. These asymptomatic subjects may have markers in their blood indicating they carry the disease, but they are totally asymptomatic.

A ssRNA virus infected subject who shows symptoms (i.e., is symptomatic) including, but not limited to, high fever, headache, joint and muscle aches, sore throat, weakness, stomach pain, lethargy, and lack of appetite, can undergo blood and/or tissue tests to confirm a diagnosis of a ssRNA virus infection. A ssRNA virus infected subject who does not show symptoms (i.e., is asymptomatic) can undergo blood and/or tissue tests to confirm a diagnosis of ssRNA virus infection. These asymptomatic subjects may have markers in their blood indicating they carry the disease, but they are totally asymptomatic.

In an embodiment, a subject can be tested for a ssRNA viral infection (e.g., but not limited to, Ebola) within a few days after symptoms begin, or after treatment according to the present disclosure, by collecting a blood or other body fluid sample and testing the sample for detection of viral antigens or RNA in blood and other body fluids using, for example, an antigen-capture enzyme-linked immunosorbent assay (ELISA), using an IgM ELISA (to determine whether the subject has IgM antibodies), using an IgG ELISA (to determine whether the subject has IgG antibodies), using polymerase chain reaction (PCR), or by virus isolation.

The present disclosure identifies agents and combinations of agents having inhibitory activity against a model filovirus. The present invention features compositions and methods for the treatment of filovirus-mediated disease, e.g., one caused by an Ebola virus or Marburg virus.

In an embodiment, the present disclosure describes a method for treating a patient with a filovirus-mediated disease, for example a disease caused by Ebola virus or Marburg virus. The method includes administering to the patient a first agent selected from the agents of Table 1, or an analog thereof, in an amount that is effective to treat the patient. In an embodiment, the method further includes administering a second agent selected from the agents of Table 1. In an embodiment, the method further includes administering a third agent selected from the agents of Table 1.

TABLE 1

| Clofazamine | Rifabutin | Clarithromycin |
|---|---|---|
| Brivudine | Aryladamantane Compounds | Upamostat |

When the methods include administering to a patient more than one active agent, the agents may be administered within 7, 6, 5, 4, 3, 2 or 1 days; within 24, 12, 6, 5, 4, 3, 2 or 1 hours, within 60, 50, 40, 30, 20, 10, 5 or 1 minutes; or substantially simultaneously. The methods of the invention may include administering one or more agents to the patient by oral, systemic, parenteral, topical, intravenous, inhalational, or intramuscular administration. In an embodiment, the methods of the invention include administering one or more agents to the patient by oral administration.

In an embodiment, the present disclosure describes a composition including two or more agents selected from the agents of Table 1. In an embodiment, the two or more agents are present in amounts that, when administered together to a patient with a filovirus-mediated disease such as a disease caused by Ebola virus or Marburg virus, are effective to treat the patient. In an embodiment, the composition consists of active ingredients and excipients, and the active ingredients consist of two or more agents selected from agents of Table 1.

Active ingredients or agents useful in the invention include those described herein in any of their pharmaceutically acceptable forms, including isomers, salts, solvates, and polymorphs thereof, as well as racemic mixtures and prodrugs.

According to aspects illustrated herein, a treatment regimen of the present disclosure is suitable to inhibit the viral replication machinery of a ssRNA virus, and is also suitable to inhibit the cytopathic effect during a ssRNA virus infection.

Small Hsps interact with a large number of client proteins that are essential to many cellular processes. For example, Hsp90 interacts with over 200 polypeptides in order to modulate their activity and/or half life. Hsp90, HspB1, and probably other small Hsps, are global regulators of cell systems. Hsp90 is a host factor for the replication of negative strand viruses and is responsible for proteins folding properly, intracellular disposition, stabilizing proteins against heat stress, and also proteolytic turnover of many essential regulators of cell growth and differentiation.

Brivudine (bromovinyldeoxyuridine or BVDU for short) interacts with two phenylalanine residues (Phe29 and Phe33) in the N-terminal domain of HspB1. The drug's full chemical description is (E)-5-(2-bromovinyl)-2-deoxyuridine. Brivudine is a nucleoside analogue targeting two viral enzymes: deoxythymidine kinases and polymerases. Brivudine is able to be incorporated into viral DNA, and then blocks the action of DNA polymerases, thus inhibiting viral replication. An oral formulation of the present disclosure including brivudine can be used an approach for a therapeutic ssRNA viral infection. The active compound is the 5'-triphosphate of BVDU, which is formed in subsequent phosphorylations by viral thymidine kinase and presumably by nucleoside diphosphate kinase. Brivudine can bind in vitro to the heat shock protein HSPB1 and inhibits interaction with its binding partners. Brivudine has properties against HSP27, HSP70 and HSP90.

A non-limiting example of the prodrug form of BVDU is represented by Formula I:

Brivudine is represented by Formula 2:

A solid oral dosage composition of the present disclosure includes (E)-5-(2-bromovinyl)2'-deoxyuridine (BVDU), a salt thereof, or BVDU in protected or in prodrug form, and at least one conventional carrier and may include at least one auxiliary material. BVDU may be present in an amount effective to produce a concentration of 0.02 µg/ml to 10.0 µg/ml in blood.

According to aspects illustrated herein, there is disclosed a composition comprising brivudine (BVDU), an active metabolite of BVDU, a salt thereof, or BVDU in protected or in prodrug form wherein brivudine (BVDU), an active metabolite of BVDU, a salt thereof, or BVDU in protected or in prodrug form is present in an amount that, when administered to a patient with a filovirus-mediated disease, is effective to treat the patient. In an embodiment, the filovirus is Ebola virus or Marburg virus.

According to aspects illustrated herein, a method for treating a patient having filovirus-mediated disease includes administering to the patient a composition comprising brivudine (BVDU), an active metabolite of BVDU, a salt thereof, or BVDU in protected or in prodrug form in an amount effective to treat the patient. In an embodiment, the filovirus is Ebola virus or Marburg virus.

Upamostat ("WX-671" or "Mesupron") inhibits the urokinase-type plasminogen activator (uPA) system. Upamostat is a serine protease inhibitor. After oral administration, serine protease inhibitor WX-671 is converted to the active Nα-(2,4,6-triisopropylphenylsulfonyl)-3-amidino-(L)-phenylalanine-4-ethoxycarbonylpiperazide ("WX-UK1"), which inhibits several serine proteases, particularly uPA. The serine protease inhibitor upamostat can potentially inhibit replication of viral RNA. An oral formulation of the present disclosure including upamostat can be used an approach for a therapeutic ssRNA viral infection. The drug's full chemical description is (S)-ethyl 4-(3-(3-(N-hydroxycarbamimidoyl)phenyl)-2-(2,4,6-triisopropylphenylsulfonamido)propanoyl) piperazine-1-carboxylate. In an embodiment of the present disclosure, upamostat is administered orally at a dose of about 0.5-to about 1.1 mg/kg. In an embodiment, upamostat is administered orally at a daily dose of between about 200 mg to 400 mg. In an embodiment, upamostat is administered orally at a daily dose of between about 150 mg to 550 mg. In an embodiment, upamostat is administered orally at a daily dose of between about 200 mg to 550 mg. In an embodiment, upamostat is administered orally at a daily dose of between about 250 mg to 550 mg. In an embodiment, upamostat is administered orally at a daily dose of between about 300 mg to 550 mg. In an embodiment, upamostat is administered orally at a daily dose of between about 350 mg to 550 mg. In an embodiment, upamostat is administered orally at a daily dose of between about 400 mg to 550 mg. In an embodiment, upamostat is administered orally at a daily dose of between about 450 mg to 550 mg. In an embodiment, upamostat is administered orally at a daily dose of between about 500 mg to 550 mg. In an embodiment, upamostat is administered orally at a daily dose of between about 200 mg to 550 mg. In an embodiment, upamostat is administered orally at a daily dose of between about 200 mg to 500 mg. In an embodiment, upamostat is administered orally at a daily dose of between about 200 mg to 450 mg. In an embodiment, upamostat is administered orally at a daily dose of between about 200 mg to 350 mg. In an embodiment, upamostat is administered orally at a daily dose of between about 200 mg to 300 mg. In an embodiment, upamostat is administered orally at a daily dose of between about 200 mg to 250 mg. In an embodiment, upamostat is administered orally at a daily dose of between about 500 mg to 1000 mg. In an embodiment, upamostat is administered orally at a daily dose of between about 750 mg to 1000 mg. In an embodiment, upamostat is administered orally at a daily dose of between about 500 mg to 750 mg.

Upamostat is represented by Formula 3:

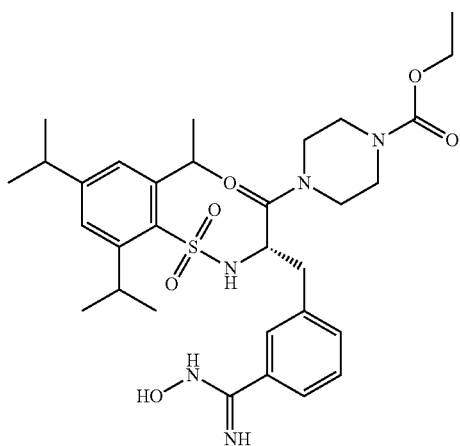

Formula 3

In an embodiment of the present disclosure, upamostat is administered orally at a dose of about 0.5-to about 1.1 mg/kg. In an embodiment, upamostat is administered orally at a daily dose of between about 200 mg to 400 mg. In an embodiment, upamostat is administered orally at a daily dose of between about 150 mg to 550 mg. In an embodiment, upamostat is administered orally at a daily dose of between about 200 mg to 550 mg. In an embodiment, upamostat is administered orally at a daily dose of between about 250 mg to 550 mg. In an embodiment, upamostat is administered orally at a daily dose of between about 300 mg to 550 mg. In an embodiment, upamostat is administered orally at a daily dose of between about 350 mg to 550 mg. In an embodiment, upamostat is administered orally at a daily dose of between about 400 mg to 550 mg. In an embodiment, upamostat is administered orally at a daily dose of between about 450 mg to 550 mg. In an embodiment, upamostat is administered orally at a daily dose of between about 500 mg to 550 mg. In an embodiment, upamostat is administered orally at a daily dose of between about 200 mg to 550 mg. In an embodiment, upamostat is administered orally at a daily dose of between about 200 mg to 500 mg. In an embodiment, upamostat is administered orally at a daily dose of between about 200 mg to 450 mg. In an embodiment, upamostat is administered orally at a daily dose of between about 200 mg to 350 mg. In an embodiment, upamostat is administered orally at a daily dose of between about 200 mg to 300 mg. In an embodiment, upamostat is administered orally at a daily dose of between about 200 mg to 250 mg. In an embodiment, upamostat is administered orally at a daily dose of between about 500 mg to 1000 mg. In an embodiment, upamostat is administered orally at a daily dose of between about 750 mg to 1000 mg. In an embodiment, upamostat is administered orally at a daily dose of between about 500 mg to 750 mg.

Clofazimine is a riminophenazine compound which can accumulate to very high concentrations in tissues. Clofazimine can inhibit bacterial growth by inducing apoptosis of host cells. Treatment with clofazimine may result in highly condensed chromatin within the nucleus, indicating macrophages undergoing apoptosis. Macrophages are responsible for a series of biochemical products with potent immunomodulatory activities. Additionally, clofazimine may stimulate the activity of various reticuloendothelial phagocytic cells. The cells, primarily monocytes and macrophages, accumulate in lymph nodes and the spleen, in connective tissues and in the liver, in lungs, and the central nervous system (microglia). The mononuclear phagocyte system is an integral part of both humoral and cell-mediated immunity and has an important role against microorganisms, including mycobacteria, fungi, and viruses.

According to aspects illustrated herein, there is disclosed a composition comprising clofazamine, wherein clofazamine is present in an amount that, when administered to a patient with a filovirus-mediated disease, is effective to treat the patient. In an embodiment, the filovirus is Ebola virus or Marburg virus. According to aspects illustrated herein, a method for treating a patient having filovirus-mediated disease includes administering to the patient a composition comprising clofazamine in an amount effective to treat the patient. In an embodiment, the filovirus is Ebola virus or Marburg virus.

In an embodiment, the dosage of clofazimine per day is from about 15 mg/day to about 120 mg/day till recovery. In an embodiment, the maximum dosage of clofazimine is 80-120 mg/day till recovery. In an embodiment, clofazimine is administered orally as a 50 mg tablet twice per day. In an embodiment, clofazimine is administered orally as a 100 mg tablet once per day. In an embodiment, clofazimine is administered as a component of a solid oral dosage form comprising from 10 mg to 16 mg of clofazimine per dosage form, for up to six times per day. In an embodiment, a method for treating a ssRNA viral infection, such as Ebola, comprises concomitantly administering: i) up to 120 mg/day of an oral clofazimine dosage form, ii) up to 450 mg/day of an oral rifabutin dosage form, iii) up to 1000 mg/day clarithromycin as either an intravenous infusion or a solid oral dosage form, and iv) up to 600 mg/day of an oral dosage form comprising brivudine, an active metabolite of brivudine, a salt thereof, or BVDU in protected or in prodrug form, wherein the administration is for a period of time until the subject is free and clear of a ssRNA viral infection, such as Ebola. Clofazimine is represented by Formula 4:

Formula 4

A ssRNA viral infection, such as Ebola virus, induces massive lymphocyte apoptosis, which is thought to prevent the development of a functional adaptive immune response. Rifabutin may be effective in inhibiting the cytopathic effect of the ssRNA viral infection, such as Ebola virus which destroys the T lymphocytes. Rifabutin interferes with RNA replication machinery by inhibiting RNA synthesis (transcription) and, consequently, the initiation of a new round of DNA replication.

According to aspects illustrated herein, there is disclosed a composition comprising rifabutin, wherein rifabutin is present in an amount that, when administered to a patient with a filovirus-mediated disease, is effective to treat the patient. In an embodiment, the filovirus is Ebola virus or Marburg virus. According to aspects illustrated herein, a method for treating a patient having filovirus-mediated disease includes administering to the patient a composition comprising rifabutin in an amount effective to treat the patient. In an embodiment, the filovirus is Ebola virus or Marburg virus.

In an embodiment, the dosage of rifabutin per day is from about 80 mg/day to about 480 mg/day. In an embodiment, the maximum dosage of rifabutin is 480 mg/day till recovery. In an embodiment, rifabutin is administered orally as a 150 mg tablet twice per day. In an embodiment, rifabutin is administered orally as a 300 mg tablet once per day. In an embodiment, rifabutin is administered as a component of a solid oral dosage form comprising from 45 mg to 60 mg of rifabutin per dosage form, for up to six times per day. In an embodiment, a method for treating a ssRNA viral infection, such as Ebola virus, comprises concomitantly administering: i) up to 450 mg/day of an oral rifabutin dosage form, ii) up to 120 mg/day of an oral clofazimine dosage form, iii) up to 1000 mg/day clarithromycin as either an intravenous infusion or a solid oral dosage form, and iv) up to 600 mg/day of an oral dosage form comprising brivudine, an active metabolite of brivudine, a salt thereof, or BVDU in protected or in prodrug form. Rifabutin is represented by Formula 5:

Formula 5

According to aspects illustrated herein, there is disclosed a composition comprising clarithromycin, wherein clarithromycin is present in an amount that, when administered to a patient with a filovirus-mediated disease, is effective to treat the patient. In an embodiment, the filovirus is Ebola virus or Marburg virus. According to aspects illustrated herein, a method for treating a patient having filovirus-mediated disease includes administering to the patient a composition comprising clarithromycin in an amount effective to treat the patient. In an embodiment, the filovirus is Ebola virus or Marburg virus.

In an embodiment, the dosage of clarithromycin per day is from about 180 mg/day to about 1000 mg/day till recovery. In an embodiment, the maximum dosage of clarithromycin is 980-1000 mg/day till recovery. In an embodiment, two doses of 500 mg clarithromycin is administered as an intravenously (IV) infusion, using a solution concentration of about 2 mg/ml. 1 gram daily of clarithromycin can be administered as an intravenously (IV) infusion for a period of from two days to five days. In an embodiment, 1 gram daily of clarithromycin can be administered as an intravenously (IV) infusion for a period of three days. In an embodiment, clarithromycin is administered orally as a 500 mg tablet twice per day. In an embodiment, clarithromycin is administered as a component of a solid oral dosage form comprising from 95 mg to 125 mg of clarithromycin per dosage form. The solid dosage form can be administered up to twelve times per day. In an embodiment, a method for treating a ssRNA viral infection, such as Ebola virus, comprises intravenously administering for a first period of time, such as for example, from 2 days to 5 days, 1 gram daily of clarithromycin followed by orally administering for a second period of time, such as from the end of the first period of time until the subject is free and clear of a ssRNA viral infection, such as Ebola virus, 1 gram daily of clarithromycin. In an embodiment, a method for treating a ssRNA viral infection, such as Ebola virus, comprises concomitantly administering: i) up to 1 gram/day of clarithromycin, ii) up to 600 mg/day of an oral dosage form comprising brivudine, an active metabolite of brivudine, a salt thereof, or BVDU in protected or in prodrug form, iii) up to 120 mg/day of an oral clofazimine dosage form, and iv) up to 450 mg/day of an oral rifabutin dosage form, wherein the administration is for a period of time until the subject is free and clear of a ssRNA viral infection, such as Ebola virus. Clarithromycin is represented by Formula 6:

Formula 6

[Chemical structure of clarithromycin]

Proinflammatory cytokines such as TNF-α, IL-1β, IL-6, IL-8, IL-12 and IFN-γ, increase vascular permeability, promote vascular leakage and the recruitment of neutrophils at the inflammatory site and stimulate the production of acute-phase proteins. In a clinical state, they induce fever or hypothermia, and peripheral shock. Co-administration of clarithromycin with clofazimine and/or rifabutin in animal models is effective at reducing pro-inflammatory cytokines such as TNF-α and IL-6 specifically. During viral infection large amounts of proinflammatory cytokines like TNF-α are secreted from macrophages. The combination of the above drugs could effectively inhibit proinflammatory cytokines and decrease the permeability of the vascular endothelium, which facilitates the virus' entry into endothelial cells.

Clarithromycin is an effective immunomodulator. Rifabutin enhances the antimicrobial and intercellular effects of clarithromycin. Additionally, clarithromycin as an immunomodulator can have considerable efficacy for patients with sepsis, as sometimes present in a ssRNA viral infection, such as Ebola virus infection. In an embodiment, clarithromycin is administered orally to a subject as a component of a solid oral dosage form. In an embodiment, clarithromycin is administered as an intravenous infusion to a subject. In an embodiment, clarithromycin may be administered as an intravenous infusion to a subject in conjunction with an oral dosage form of Brivudine (BVDU), an active metabolite of BVDU, a salt thereof, or BVDU in protected or in prodrug form. In an embodiment, clarithromycin may be administered as an intravenous infusion to a subject in conjunction with an oral dosage form of upamostat.

According to aspects illustrated herein, there is disclosed a composition comprising rifabutin and clarithromycin, wherein rifabutin and clarithromycin are present in amounts that, when administered together to a patient with a filovirus-mediated disease, are effective to treat the patient. In an embodiment, the filovirus is Ebola virus or Marburg virus. According to aspects illustrated herein, a method for treating a patient having filovirus-mediated disease includes administering to the patient a composition comprising rifabutin and clarithromycin in amounts effective to treat the patient. In an embodiment, the filovirus is Ebola virus or Marburg virus.

According to aspects illustrated herein, there is disclosed a composition comprising clofazamine, rifabutin and clarithromycin, wherein clofazamine, rifabutin and clarithromycin are present in amounts that, when administered together to a patient with a filovirus-mediated disease, are effective to treat the patient. In an embodiment, the filovirus is Ebola virus or Marburg virus. According to aspects illustrated herein, a method for treating a patient having filovirus-mediated disease includes administering to the patient a composition comprising clofazamine, rifabutin and clarithromycin in amounts effective to treat the patient. In an embodiment, the filovirus is Ebola virus or Marburg virus.

In an embodiment, rifabutin, clarithromycin, and clofazimine are administered as a single solid oral dosage form. In an embodiment, a solid oral dosage form of the present disclosure comprises rifabutin, clarithromycin, clofazimine, and a pharmaceutically acceptable carrier, wherein the amount of clofazimine is 5-18% w/w relative to the amount of clarithromycin (such as, 7-16%, 9-14%, 9-12%, 10-15%, or 0-11% w/w) and 10-25% w/w relative to the amount of rifabutin (such as, 12-25%, 12-23%, 15-25%, 15-23%, 18-25%, 18-23%, 20-25%, 20-23%, or 21-23%).

In an embodiment, a solid oral dosage form of the present disclosure comprises rifabutin, clarithromycin, and clofazimine in an 8-10:18-20:1-2.5 w/w/w ratio (for example, a 8.5-9.5:18.5-19.5:1.5-2.5 w/w/w ratio or a 9:19:2 ratio, wherein each variable is free to vary ±0.5 or 0.25). In an embodiment, a solid oral dosage form of the present disclosure comprises rifabutin, clarithromycin, and clofazimine in about a 9:19:2 w/w/w ratio, wherein each of the variables are free to vary ±2, 1, 0.5, or 0.25 (e.g., 9±0.5:19±5:21.0.5). For example in an embodiment, a solid oral dosage form of the present disclosure comprises 90 mg rifabutin (±30, 20, 10, 5, 2, or 1 mg), 190 mg clarithromycin (±60, 40, 20, 10, 5, 2, or 1 mg), and 20 mg clofazimine (±10, 7, 5, 2, or 1 mg). In an embodiment, a solid oral dosage form of the present disclosure comprises 45 mg rifabutin (±15, 10, 7, 5, 2, or 1 mg), 95 mg clarithromycin (±30, 20, 10, 5, 2, or 1 mg), and 10 mg clofazimine (±6, 5, 2, or 1 mg).

In embodiment, a solid oral dosage form of the present disclosure further comprises an absorption enhancer that may improve bioavailability of one or more of the active ingredients. The amount of absorption enhancer may between 300-700% w/w relative to the amount of clofazimine including 400-600% or 450-550% or 475-525%. In certain embodiments, the absorption enhancer is polyethylene glycol (PEG), for example, polyethylene glycol having an average molecular weight of between 200-20,000 including between 1000-15000 or 5000-12000 or 7000-9000 or 7500-8500, for example PEG 8000).

In embodiment, a solid oral dosage form of the present disclosure further comprises one or more additional excipients, such as MCC-Tabulose type 200, Mg Stearate, SLS-Emal 10Pwd HD, a polysorbate (such as, polysorbate 80), or a combination thereof, including all of these. In some instances, the present compositions include both polyethylene glycol and a polysorbate, such as polysorbate 80, wherein the amount of polysorbate is 30-120% w/w relative to the amount of clofazimine (such as 50-100%, 50-85%, or 60-75%).

In an embodiment, a solid oral dosage form of the present disclosure further comprises one or more additional excipients, such as Microcrystalline cellulose (MCC) TABULOSE® SC 200), Mg Stearate, Sodium Lauryl Sulfate (SLS) EMAL® 10Pwd HD, a polysorbate (such as, polysorbate 80), or a combination thereof, including all of these. In some instances, the present compositions include both polyethylene glycol and a polysorbate, such as polysorbate 80, wherein the amount of polysorbate is 30-120% w/w relative to the amount of clofazimine (such as 50-100%, 50-85%, or 60-75%).

In an embodiment, a solid oral dosage form of the present disclosure is available in the form of a tablet or a capsule containing an active in a powdered form. In an embodiment, a solid oral dosage form of the present disclosure is in the form of a tablet or a capsule containing an active in a microencapsulated form. In an embodiment, a solid oral dosage form of the present disclosure is in the form of a tablet or a capsule containing an active in a microgranulated form.

In an embodiment, a solid oral dosage form of the present disclosure is available in the form of a tablet comprising at least one of rifabutin, clarithromycin, and clofazimine in a powdered form. In some instances two or all of rifabutin, clarithromycin, and clofazimine are in a powdered form. In an embodiment, a solid oral dosage form of the present disclosure is in the form of a tablet or a capsule comprising at least one of rifabutin, clarithromycin, and clofazimine in a microencapsulated form. In some instances, two or all of rifabutin, clarithromycin, and clofazimine are in a microencapsulated form. In an embodiment, a solid oral dosage form of the present disclosure is in the form of a tablet or a capsule comprising at least one of rifabutin, clarithromycin, and clofazimine in a powdered form, and the remaining agents present in a microencapsulated form. In an embodiment, a solid oral dosage form of the present disclosure is in the form of a tablet or a capsule comprising one or more of rifabutin, clarithromycin, and clofazimine in a microgranulated form. In an embodiment, a solid oral dosage form of the present disclosure is in the form of a tablet comprising one or more of rifabutin, clarithromycin, and clofazimine within a capsule, a capsule containing one or more of rifabutin, clarithromycin, and clofazimine within a tablet, a capsule containing one or more of rifabutin, clarithromycin, and clofazimine within an outer capsule containing the other agents, or any combination of the above. In an embodiment, a solid oral dosage form of the present disclosure comprises an inner capsule containing rifabutin, within an outer capsule containing clarithromycin and clofazimine, wherein clarithromycin and clofazimine may be present in powdered, microencapsulated, or microgranulated forms.

Surprisingly, concomitant administration of multiple drugs disclosed herein, including, but not limited to concomitant administration of brivudine with at least one of clofazimine, rifabutin, clarithromycin, or upamostat, can inhibit the replication machinery of a ssRNA virus infection so as to hinder, restrain or prevent viral infection.

Surprisingly, concomitant administration of multiple drugs disclosed herein, including, but not limited to concomitant administration of brivudine with at least one of clofazimine, rifabutin, clarithromycin, or upamostat, can inhibit the replication machinery of a ssRNA virus infection so as to hinder, restrain or prevent viral infection.

Surprisingly, concomitant administration of multiple drugs disclosed herein, including, but not limited to concomitant administration of brivudine with at least one of clofazimine, rifabutin, clarithromycin, or upamostat, can inhibit the cytopathic effect of a ssRNA virus infection so as to hinder, restrain or prevent degenerative changes or abnormalities.

According to aspects illustrated herein, there is disclosed a composition comprising rifabutin, clarithromycin, and brivudine wherein rifabutin, clarithromycin and brivudine are present in amounts that, when administered together to a patient with a filovirus-mediated disease, are effective to treat the patient. In an embodiment, the filovirus is Ebola virus or Marburg virus.

According to aspects illustrated herein, a method for treating a patient having filovirus-mediated disease includes administering to the patient a composition comprising rifabutin, clarithromycin and Brivudine in amounts effective to treat the patient. In an embodiment, the filovirus is Ebola virus or Marburg virus.

According to aspects illustrated herein, a method for treating a subject having a ssRNA viral infection includes concomitant administration of a therapeutically effective amount of brivudine (BVDU), an active metabolite of BVDU, a salt thereof, or BVDU in protected or in prodrug form; a therapeutically effective amount of rifabutin; and a therapeutically effective amount of clarithromycin.

According to aspects illustrated herein, a method for treating a subject having a ssRNA viral infection includes concomitant administration as follows: orally administering a tablet comprising a therapeutically effective amount of brivudine (BVDU), an active metabolite of BVDU, a salt thereof, or BVDU in protected or in prodrug form; orally administering a capsule or tablet comprising rifabutin; and orally administering a capsule or tablet comprising clarithromycin, wherein the rifabutin and the clarithromycin may be present in the same capsule or tablet.

According to aspects illustrated herein, a method for treating a subject having a ssRNA viral infection includes concomitant administration as follows: orally administering a therapeutically effective amount of brivudine (BVDU), an active metabolite of BVDU, a salt thereof, or BVDU in protected or in prodrug form for a suitable period of time; and administering a therapeutically effective amount of at least one of clofazimine, rifabutin or clarithromycin, for a suitable period of time. In an embodiment, a therapeutically effective amount of BVDU is up to 600 mg/day for an adult. In an embodiment, the 600 mg is administered once daily as a single oral dosage form. In an embodiment, the 600 mg is administered as a 150 mg single oral dosage form taken four times daily. In an embodiment, a therapeutically effective amount of BVDU is up to 500 mg/day for an adult. In an embodiment, the 500 mg is administered once daily as a single oral dosage form. In an embodiment, the 500 mg is administered as a 125 mg single oral dosage form taken four times daily. In an embodiment, the therapeutically effective amount of clofazimine is from about 50 mg to about 300 mg daily for an adult. In an embodiment, clofazimine is administered orally as a solid dosage form one or more times per day. In an embodiment, the therapeutically effective amount of rifabutin is from about 45 mg to about 480 mg daily for an adult. In an embodiment, rifabutin is administered orally as a solid dosage form one or more times per day. In an embodiment, the therapeutically effective amount of clofazimine is from about 50 mg to about 300 mg daily for an adult. In an embodiment, clofazimine is administered orally as a solid dosage form one or more times per day.

According to aspects illustrated herein, a method for treating a subject having a ssRNA viral infection includes concomitant administration as follows: orally administering a therapeutically effective amount of brivudine (BVDU), an active metabolite of BVDU, a salt thereof, or BVDU in protected or in prodrug form for a suitable period of time; and orally administering a therapeutically effective amount of a solid oral dosage form that comprises at least one of clofazimine or rifabutin for a suitable period of time; and administering a therapeutically effective amount of clarithromycin as an intravenous infusion for a suitable period of time. In an embodiment, a therapeutically effective amount of BVDU is up to 600 mg/day for an adult. In an embodiment, the 600 mg is administered once daily as a single oral dosage form. In an embodiment, the 600 mg is administered as a 150 mg single oral dosage form taken four times daily. In an embodiment, a therapeutically effective amount of BVDU is up to 500 mg/day for an adult. In an embodiment, the 500 mg is administered once daily as a single oral dosage form. In an embodiment, the 500 mg is administered as a 125 mg single oral dosage form taken four times daily. In an embodiment, a therapeutically effective amount of clarithromycin is up to 1 gram daily for an adult. In an embodiment, two doses of 500 mg clarithromycin is administered as an IV infusion, using a solution concentration of about 2 mg/ml. 1 gram daily of clarithromycin can be administered as an IV infusion for a period of from two days to five days. In an embodiment, 1 gram daily of clarithromycin can be administered as an IV infusion for a period of three days. In an embodiment, a therapeutically effective amount of rifabutin is up to 480 mg daily for an adult. In an embodiment, rifabutin is administered orally as a tablet one or more times per day. In an embodiment, rifabutin is administered as a component of a solid oral dosage form comprising from 45 mg to 60 mg of rifabutin per dosage form. A solid dosage form comprising from 45 mg to 60 mg of rifabutin can be administered up to twelve times per day. In an embodiment, a therapeutically effective amount of clofazimine is from about 50 mg to about 300 mg daily for an adult. In an embodiment, clofazimine is administered orally as a solid dosage form one or more times per day. In an embodiment, clofazimine is administered as a component of a solid oral dosage form comprising from 10 mg to 16 mg of clofazimine per dosage form.

According to aspects illustrated herein, a method for treating a subject having a ssRNA viral infection includes concomitant administration as follows: orally administering a therapeutically effective amount of brivudine (BVDU), an active metabolite of BVDU, a salt thereof, or BVDU in protected or in prodrug form for a suitable period of time; and administering a therapeutically effective amount of clarithromycin as an intravenous infusion for a suitable period of time. In an embodiment, a therapeutically effective amount of BVDU is up to 600 mg/day for an adult. In an embodiment, the 600 mg is administered once daily as a single oral dosage form. In an embodiment, the 600 mg is administered as a 150 mg single oral dosage form taken four times daily. In an embodiment, a therapeutically effective amount of BVDU is up to 500 mg/day for an adult. In an embodiment, the 500 mg is administered once daily as a single oral dosage form. In an embodiment, the 500 mg is administered as a 125 mg single oral dosage form taken four times daily. In an embodiment, the therapeutically effective amount of clarithromycin is up to 1 gram daily for an adult. The clarithromycin is administered as an intravenous (IV) infusion. In an embodiment, two doses of 500 mg clarithromycin is administered as an IV infusion, using a solution concentration of about 2 mg/ml. 1 gram daily of clarithromycin can be administered as an IV infusion for a period of from two days to five days. In an embodiment, 1 gram daily of clarithromycin can be administered as an IV infusion for a period of three days.

According to aspects illustrated herein, a method for treating a subject having a ssRNA viral infection includes concomitant administration as follows: orally administering a therapeutically effective amount of brivudine (BVDU), an active metabolite of BVDU, a salt thereof, or BVDU in protected or in prodrug form for a suitable period of time; orally administering a therapeutically effective amount of a solid oral dosage form that comprises clarithromycin for a suitable period of time; orally administering a therapeutically effective amount of a solid oral dosage form that comprises rifabutin for a suitable period of time; and orally administering a therapeutically effective amount of a solid oral dosage form that comprises clofazimine, for a suitable period of time. In an embodiment, a therapeutically effective amount of BVDU is up to 600 mg/day for an adult. In an embodiment, the 600 mg is administered once daily as a single oral dosage form. In an embodiment, the 600 mg is administered as a 150 mg single oral dosage form taken four times daily. In an embodiment, a therapeutically effective amount of BVDU is up to 500 mg/day for an adult. In an embodiment, the 500 mg is administered once daily as a single oral dosage form. In an embodiment, the 500 mg is administered as a 125 mg single oral dosage form taken four times daily. In an embodiment, a therapeutically effective amount of clarithromycin is up to 1 gram daily for an adult. In an embodiment, clarithromycin is administered orally as a 500 mg tablet twice per day. In an embodiment, a therapeutically effective amount of rifabutin is up to 480 mg daily for an adult. In an embodiment, rifabutin is administered orally as a tablet one or more times per day. In an embodiment, rifabutin is administered as a component of a solid oral dosage form comprising from 45 mg to 60 mg of rifabutin per dosage form. A solid dosage form comprising from 45 mg to 60 mg of rifabutin can be administered up to twelve times per day. In an embodiment, a therapeutically effective amount of clofazimine is from about 50 mg to about 300 mg daily for an adult. In an embodiment, clofazimine is administered orally as a solid dosage form one or more times per day. In an embodiment, clofazimine is administered as a component of a solid oral dosage form comprising from 10 mg to 16 mg of clofazimine per dosage form.

In an embodiment, clofazimine and brivudine are administered orally as a solid dosage form one or more times per day. In an embodiment, clofazimine, rifabutin, and brivudine are administered orally as a solid dosage form one or more times per day. In an embodiment, rifabutin and brivudine are administered orally as a solid dosage form one or more times per day. In an embodiment, clarithromycin, rifabutin, and brivudine are administered orally as a solid dosage form one or more times per day. In an embodiment, clarithromycin, clofazimine, and brivudine are administered orally as a solid dosage form one or more times per day. In an embodiment, upamostat, clofazimine, and brivudine are administered orally as a solid dosage form one or more times per day. In an embodiment, upamostat, rifabutin, clofazimine, and brivudine are administered orally as a solid dosage form one or more times per day. In an embodiment, upamostat, rifabutin, and brivudine are administered orally as a solid dosage form one or more times per day. In an embodiment, upamostat, rifabutin, clarithromycin, and brivudine are administered orally as a solid dosage form one or more times per day. In an embodiment, upamostat, brivudine, clarithromycin, and clofazimine are administered orally as a solid dosage form one or more times per day. In an embodiment, upamostat, brivudine, clarithromycin, rifabutin, and clofazimine are administered orally as a solid dosage form one or more times per day.

In an embodiment, the rifabutin, clarithromycin and clofazimine are administered as a single solid oral dosage form. In some instances, the rifabutin, clarithromycin, and clofazimine are co-administered once each day for a first period of treatment (for example, 1-3 weeks, including 1 week, 2 weeks or three weeks) in the following amounts: (i) 80-100 mg rifabutin (such as, 85-95 mg or 90 mg±1.5 mg), (ii) 180-200 mg clarithromycin (such as, 185-195 mg or 190 mg±2 mg), and (iii) 15-25 mg clofazimine (such as 17-23 mg or 20±1 mg). The method may further include the step of linearly increasing the amounts of the rifabutin, clarithromycin, and clofazimine while maintaining a 8-10:18-20:1-2.5 w/w/w ratio (for example, a 8.5-9.5:18.5-19.5:1.5-2.5 w/w/w ratio or a 9:19:2 ratio, wherein each variable is free to vary ±0.5 or 0.25 ratio) for a second period of treatment (for example, from 4-10 weeks). In an embodiment, the linearly increasing amounts of the rifabutin, clarithromycin, and clofazimine do not exceed maximum amounts of (i) 420-480 mg rifabutin (such as, 440-460 mg or 450 mg), 920-980 mg clarithromycin (such as, 940-960 mg or 950 mg), and (iii) 80-120 mg clofazimine (such as, 90-110 mg or 100 mg) during the second period of treatment. In certain instances, the linearly increasing amounts of rifabutin, clarithromycin, and clofazimine comprise: a) (i) 160-200 mg rifabutin (such as, 170-190 mg or 180 mg±2 mg), (ii) 360-400 mg clarithromycin (such as, 370-390 mg or 380 mg±2 mg), and (iii) 30-50 mg clofazimine (such as, 35-45 mg or 40 mg±1 mg) once each day for two weeks; b) (i) 250-290 mg rifabutin (such as, 260-280 mg or 270 mg±2 mg), (ii) 550-590 mg clarithromycin (such as, 560-580 mg or 570±2 mg), and (iii) 50-70 mg clofazimine (such as, 55-65 mg or 60 mg±1.5 mg) once each day for two weeks; c) (i) 340-380 mg rifabutin (such as, 350-370 mg or 360 mg±2 mg), (ii) 740-780 mg clarithromycin (such as 750-770 mg or 760 mg±2 mg), and (iii) 60-100 mg clofazimine (such as, 70-90 mg or 80 mg±1.5 mg) once each day for two weeks; and d) (i) 420-480 mg rifabutin (such as, 440-460 mg or 450 mg±2 mg), (ii) 920-980 mg clarithromycin (such as, 940-960 mg or 950 mg±2 mg), and (iii) 80-120 mg clofazimine (such as, 90-110 mg or 100 mg±1.5 mg) once each day for a week. In certain embodiments, the method further includes, following step d) above, the step of simultaneously co-administering (i) 420-480 mg rifabutin (such as, 440-460 mg or 450 mg±2 mg), (ii) 920-980 mg clarithromycin (such as, 940-960 mg or 950 mg±2 mg), and (iii) 80-120 mg clofazimine (such as, 90-110 mg or 100 mg±1.5 mg) once each day for a third period of treatment. In some embodiments, the third period of treatment is 1, 2, 4, 6, 8, 12 weeks; 3, 6, or 12 months or longer. In one embodiment the third period of treatment continues until either a reduction in symptoms associated with a ssRNA viral infection or due to a laboratory diagnosis indicating that the a ssRNA viral disease is under control.

In an embodiment, the single solid oral dosage form includes rifabutin; clarithromycin; clofazimine; an absorption enhancer; and a pharmaceutically acceptable carrier, wherein the pharmaceutical composition is a solid oral dosage form, wherein the absorption enhancer is between 300% and 700% w/w relative to the amount of clofazimine, and wherein an amount of clofazimine is 10-15% w/w relative to an amount of clarithromycin and 20-25% w/w relative to an amount of rifabutin.

In an embodiment, the single solid oral dosage form includes rifabutin; clarithromycin; clofazimine; polyethylene glycol; and a pharmaceutically acceptable carrier, wherein the pharmaceutical composition is a solid oral dosage form, wherein the polyethylene glycol, (i) has an average molecular weight of between 1000-15000 Daltons, and (ii) is between 300% and 700% w/w relative to the amount of clofazimine, and wherein an amount of clofazimine is 10-15% w/w relative to an amount of clarithromycin and 20-25% w/w relative to an amount of rifabutin.

Small heat shock proteins (small Hsps) are stress-induced molecular chaperones that act as holdases towards polypeptides that have lost their folding in stress conditions or consequently of mutations in their coding sequence. A cellular protection against the deleterious effects mediated by damaged proteins is thus provided to cells. These chaperones are also highly expressed in response to protein conformational and inflammatory diseases and cancer pathologies. Through specific and reversible modifications in their phospho-oligomeric organization, small Hsps can chaperone appropriate client proteins in order to provide cells with resistance to different types of injuries or pathological conditions. By helping cells to better cope with their pathological status, their expression can be either beneficial, such as in diseases characterized by pathological cell degeneration, or deleterious when they are required for tumor cell survival. Moreover, small Hsps are actively released by cells and can act as immunogenic molecules that have dual effects depending on the pathology. Five families of Hsps are induced by stress: the 70 kDa (HspA-Hsp70) family, the 20-30 kDa (HspB-small Hsps, sHsps) family, the 90 kDa (HspC-Hsp90) family, the 60 kDa (HspD-Hsp60) family, and the HspH (large Hsps) family.

An aryladamantane compound of the present invention has been shown to be capable of selectively inhibiting SK2 activity in vitro. Without being bound by theory, it is believed that inhibition of sphingosine kinase (SK) may impair viral protein expression and infectious virus production from cells expressing a cellular protein that acts as a receptor for Ebola virus and Marburg virus. According to aspects illustrated herein, there is disclosed a composition comprising an aryladamantane compound, wherein the aryladamantane compound is present in an amount that, when administered to a patient with a filovirus-mediated disease, are effective to treat the patient. In an embodiment, the filovirus is Ebola virus or Marburg virus. According to aspects illustrated herein, a method for treating a patient having filovirus-mediated disease includes administering to the patient a composition comprising an aryladamantane compound in an amount effective to treat the patient. In an embodiment, the filovirus is Ebola virus or Marburg virus.

The symbol "—" in general represents a bond between two atoms in the chain. Thus $CH_3$—O—$CH_2$—$CH(R_i)$—$CH_3$ represents a 2-substituted-1-methoxypropane compound. In addition, the symbol "—" represents the point of attachment of the substituent to a compound. Thus for example aryl($C_1$-$C_6$)alkyl- indicates an alkylaryl group, such as benzyl, attached to the compound at the alkyl moiety.

Where multiple substituents are indicated as being attached to a structure, it is to be understood that the substituents can be the same or different. Thus for example "$R_m$ optionally substituted with 1, 2 or 3 $R_q$ groups" indicates that $R_m$ is substituted with 1, 2, or 3 $R_q$ groups where the $R_q$ groups can be the same or different.

The phrase "optionally substituted" is used interchangeably with the phrase "substituted or unsubstituted". Unless otherwise indicated, an optionally substituted group may have a substituent at each substitutable position of the group, and each substituent is independent of the other.

As used herein, the terms "halogen" or "halo" indicate fluorine, chlorine, bromine, or iodine.

The term "heteroatom" means nitrogen, oxygen or sulfur and includes any oxidized form of nitrogen and sulfur, and the quaternized form of any basic nitrogen. Also the term "nitrogen" includes a substitutable nitrogen in a heterocyclic ring. As an example, in a saturated or partially unsaturated ring having 0-3 heteroatoms selected from nitrogen, oxygen or sulfur, the nitrogen may be N (as in 3,4-dihydro-2H-pyrrolyl), NH (as in pyrrolidinyl) or NR$^+$ (as in N-substituted pyrrolidinyl).

The term "alkyl", as used herein alone or as part of a larger moiety, refers to a saturated aliphatic hydrocarbon including straight chain, branched chain or cyclic (also called "cycloalkyl") groups. Examples of alkyl groups include methyl, ethyl, propyl, isopropyl, butyl, iso-, sec- and tert-butyl, pentyl, hexyl, heptyl, 3-ethylbutyl, and the like. Preferably, the alkyl group has 1 to 20 carbon atoms (whenever a numerical range, e.g. "1-20", is stated herein, it means that the group, in this case the alkyl group, may contain 1 carbon atom, 2 carbon atoms, 3 carbon atoms, etc. up to and including 20 carbon atoms). More preferably, it is a medium size alkyl having 1 to 10 carbon atoms. Most preferably, it is a lower alkyl having 1 to 4 carbon atoms. The cycloalkyl can be monocyclic, or a polycyclic fused system. Examples of cycloalkyl groups include cyclopropyl, cyclobutyl, cycolpentyl, cyclohexyl, cycloheptyl, cyclooctyl, and adamantyl. The alkyl or cycloalkyl group may be unsubstituted or substituted with 1, 2, 3 or more substituents. Examples of such substituents including, without limitation, halo, hydroxy, amino, alkoxy, alkylamino, dialkylamino, cycloalkly, aryl, aryloxy, arylalkyloxy, heterocyclic radical, and (heterocyclic radical)oxy. Examples include fluoromethyl, hydroxyethyl, 2,3-dihydroxyethyl, (2- or 3-furanyl) methyl, cyclopropylmethyl, benzyloxyethyl, (3-pyridinyl) methyl, (2-thienyl)ethyl, hyroxypropyl, aminocyclohexyl, 2-dimethylaminobutyl, methoxymethyl, N-pyridinyl ethyl, and diethylaminoethyl.

The term "cycloalkylalkyl", as used herein alone or as part of a larger moiety, refers to a $C_3$-$C_{10}$ cycloalkyl group attached to the parent molecular moiety through an alkyl group, as defined above. Examples of cycloalkylalkyl groups include cyclopropylmethyl and cyclopentylethyl.

The term "alkenyl", as used herein alone or as part of a larger moiety, refers to an aliphatic hydrocarbon having at least one carbon-carbon double bond, including straight chain, branched chain or cyclic groups having at least one carbon-carbon double bond. Preferably, the alkenyl group has 2 to 20 carbon atoms. More preferably, it is a medium size alkenyl having 2 to 10 carbon atoms. Most preferably, it is a lower alkenyl having 2 to 6 carbon atoms. The alkenyl group may be unsubstituted or substituted with 1, 2, 3 or more substituents. Examples of such substituents including, without limitation halo, hydroxy, amino, alkoxy, alkylamino, dialkylamino, cycloalkly, aryl, aryloxy, arylalkyloxy, heterocyclic radical, and (heterocyclic radical)oxy. Depending on the placement of the double bond and substituents, if any, the geometry of the double bond may be entgegen (E) or zusammen (Z), cis, or trans. Examples of alkenyl groups include ethenyl, propenyl, cis-2-butenyl, trans-2-butenyl, and 2-hyroxy-2-propenyl.

The term "alkynyl", as used herein alone or as part of a larger moiety, refers to an aliphatic hydrocarbon having at least one carbon-carbon triple bond, including straight chain, branched chain or cyclic groups having at least one carbon-carbon triple bond. Preferably, the alkynyl group has 2 to 20 carbon atoms. More preferably, it is a medium size alkynyl having 2 to 10 carbon atoms. Most preferably, it is a lower alkynyl having 2 to 6 carbon atoms. The alkynyl group may be unsubstituted or substituted with 1, 2, 3 or more substituents. Examples of such substituents including, without limitation, halo, hydroxy, amino, alkoxy, alkylamino, dialkylamino, cycloalkly, aryl, aryloxy, arylalkyloxy, heterocyclic radical, and (heterocyclic radical)oxy. Examples of alkynyl groups include ethynyl, propynyl, 2-butynyl, and 2-hyroxy-3-butylnyl.

The term "alkoxy", as used herein alone or as part of a larger moiety, represents an alkyl group of indicated number of carbon atoms attached to the parent molecular moiety through an oxygen bridge. Examples of alkoxy groups include, for example, methoxy, ethoxy, propoxy and isopropoxy. Alkoxy radicals may be further substituted with one or more halo atoms, such as fluoro, chloro or bromo, to provide "haloalkoxy" radicals. Examples of such radicals include fluoromethoxy, chloromethoxy, trifluoromethoxy, and fluoroethoxy.

The term "aryl", as used herein alone or as part of a larger moiety, refers to an aromatic hydrocarbon ring system containing at least one aromatic ring. The aromatic ring may optionally be fused or otherwise attached to other aromatic hydrocarbon rings or non-aromatic hydrocarbon rings. Additionally, the aryl group may be substituted or unsubstituted by various groups such as hydrogen, halo, hydroxy, alkyl, haloalkyl, alkoxy, nitro, cyano, alkylamine, carboxy or alkoxycarbonyl. Examples of aryl groups include, for example, phenyl, naphthyl, 1,2,3,4-tetrahydronaphthalene, benzodioxole, and biphenyl. Preferred examples of unsubstituted aryl groups include phenyl and biphenyl. Preferred aryl group substituents include hydrogen, halo, alkyl, haloalkyl, hydroxy and alkoxy.

The term "heteroalkyl", as used herein alone or as part of a larger moiety, refers to an alkyl radical as defined herein with one or more heteroatoms replacing a carbon atom with the moiety. Such heteroalkyl groups are alternately referred to using the terms ether, thioether, amine, and the like.

The term "heterocyclyl", as used herein alone or as part of a larger moiety, refers to saturated, partially unsaturated and unsaturated heteroatom-containing ring shaped radicals, where the heteroatoms may be selected from nitrogen, sulfur and oxygen. Said heterocyclyl groups may be unsubstituted or substituted at one or more atoms within the ring system. The heterocyclic ring may contain one or more oxo groups.

The term "heterocycloalkyl", as used herein alone or as part of a larger moiety, refers to a non-aromatic ring system containing at least one heteroatom selected from nitrogen, oxygen, and sulfur. The heterocycloalkyl ring may be optionally fused to or otherwise attached to other heterocycloalkyl rings and/or non-aromatic hydrocarbon rings. Preferred heterocycloalkyl groups have from 3 to 7 members. Examples of heterocycloalkyl groups include, for example, piperazine, morpholine, piperidine, tetrahydrofuran, pyrrolidine, and pyrazole. Preferred monocyclic heterocycloalkyl groups include piperidyl, piperazinyl, morpholinyl, pyrrolidinyl, thiomorpholinyl, thiazolidinyl, 1,3-dioxolanyl, 1,4-dioxanyl, tetrahydrofuranyl, tetrahydrothiophenyl, tetrahydrothiopyranyl, and the like. Heterocycloalkyl radicals may also be partially unsaturated. Examples of such groups include dihydrothienyl, dihydropyranyl, dihydrofuryl, and dihydrothiazolyl.

The term "heteroaryl", as used herein alone or as part of a larger moiety, refers to an aromatic ring system containing at least one heteroatom selected from nitrogen, oxygen, and sulfur. The heteroaryl ring may be fused or otherwise attached to one or more heteroaryl rings, aromatic or non-aromatic hydrocarbon rings or heterocycloalkyl rings. Additionally, the heteroaryl group may be unsubstituted or substituted at one or more atoms of the ring system, or may contain one or more oxo groups. Examples of heteroaryl groups include, for example, pyridine, furan, thiophene, carbazole and pyrimidine. Preferred examples of heteroaryl groups include thienyl, benzothienyl, pyridyl, quinolyl, pyrazinyl, pyrimidyl, imidazolyl, benzimidazolyl, furanyl, benzofuranyl, thiazolyl, benzothiazolyl, isoxazolyl, oxadiazolyl, isothiazolyl, benzisothiazolyl, triazolyl, tetrazolyl, pyrrolyl, indolyl, pyrazolyl, benzopyrazolyl, purinyl, benzooxazolyl, and carbazolyl.

The tem "acyl" means an H—C(O)— or alkyl-C(O)— group in which the alkyl group, straight chain, branched or cyclic, is as previously described. Exemplary acyl groups include formyl, acetyl, propanoyl, 2-methylpropanoyl, butanoyl, and caproyl.

The term "aroyl" means an aryl-C(O)— group in which the aryl group is as previously described. Exemplary aroyl groups include benzoyl and 1- and 2-naphthoyl.

The term "solvate" means a physical association of a compound of this invention with one or more solvent molecules. This physical association involves varying degrees of ionic and covalent bonding, including hydrogen bonding. In certain instances, the solvate will be capable of isolation, for example when one or more solvent molecules are incorporated in the crystal lattice of the crystalline solid. "Solvate" encompasses both solution-phase and isolatable solvates. Exemplary solvates include ethanolates, methanolates, and the like. "Hydrate" is a solvate wherein the solvent molecule(s) is/are $H_2O$.

Examples of aryladamantane compound of the present invention are generally represented by Formula 7, shown below:

Formula 7

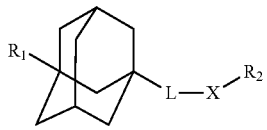

(I)

and pharmaceutically acceptable salts thereof, wherein
L is a bond or is —C—($R_3$,$R_4$)—;
X is —($R_3$,$R_4$)N($R_5$)—, —C(O)N($R_4$)—, —N($R_4$)C(O)—, —C($R_4$,$R_5$)—, —N($R_4$)—, —O—, —S—, —C(O)—, —S(O)$_2$—, —S(O)$_2$N($R_4$)—, or —N($R_4$)S(O)$_2$—;
$R_1$ is H, alkyl, cycloalkyl, cycloalkylalkyl, alkenyl, alkynyl, heteroalkyl, aryl, alkylaryl, alkenylaryl, heterocyclyl, heteroaryl, alkylheteroaryl, heterocycloalkyl, alkyl-heterocycloalkyl, acyl, aroyl, halogen, haloalkyl, alkoxy, haloalkoxy, hydroxyalkyl, alkanoyl, —COOH, —OH, —SH, —S-alkyl, —CN, —NO$_2$, —NH$_2$, —CO$_2$(alkyl), —OC(O)alkyl, carbamoyl, mono or dialkylaminocarbamoyl, mono or dialkylcarbamoyl, mono or dialkylamino, aminoalkyl, mono- or dialkylaminoalkyl, thiocarbamoyl, or mono or dialkylthiocarbamoyl;
$R_2$ is H, alkyl, cycloalkyl, cycloalkylalkyl, alkenyl, alkynyl, heteroalkyl, aryl, alkylaryl, alkenylaryl, heterocyclyl, heteroaryl, alkylheteroaryl, heterocycloalkyl, alkyl-heterocycloalkyl, acyl, aroyl, halogen, haloalkyl, alkoxy, haloalkoxy, hydroxyalkyl, alkanoyl, —COOH, —OH, —SH, —S-alkyl, —CN, —NO$_2$, —NH$_2$, —CO$_2$(alkyl), —OC(O)alkyl, carbamoyl, mono or dialkylaminocarbamoyl, mono or dialkylcarbamoyl, mono or dialkylamino, aminoalkyl, mono- or dialkylaminoalkyl, thiocarbamoyl, mono or dialkylthiocarbamoyl, alkyl-S-alkyl, -heteroaryl-aryl, -alkyl-heteroarylaryl, —C(O)—NH-aryl, -alkenyl-heteroaryl, —C(O)-heteroaryl, or -alkenyl-heteroaryl-aryl;
$R_3$ is H, alkyl, cycloalkyl, cycloalkylalkyl, alkenyl, alkynyl, heteroalkyl, aryl, alkylaryl, alkenylaryl, heterocyclyl, heteroaryl, alkylheteroaryl, heterocycloalkyl, alkyl-heterocycloalkyl, acyl, aroyl, halogen, haloalkyl, alkoxy, haloalkoxy, hydroxyalkyl, alkanoyl, oxo (=O), —COOH, —OH, —SH, —S-alkyl, —CN, —NO$_2$, —NH$_2$, —CO$_2$(alkyl), —OC(O)alkyl, carbamoyl, mono or dialkylaminocarbamoyl, mono or dialkylcarbamoyl, mono or dialkylamino, aminoalkyl, mono- or dialkylaminoalkyl, thiocarbamoyl, or mono or dialkylthiocarbamoyl;
wherein the alkyl and ring portion of each of the above $R_1$, $R_2$, and $R_3$ groups is optionally substituted with up to 5 groups that are independently ($C_1$-$C_6$) alkyl, halogen, haloalkyl, —OC(O)($C_1$-$C_6$ alkyl), —C(O)O($C_1$-$C_6$ alkyl), —CONR'R", —OC(O)NR'R", —NR'C(O)R", —CF$_3$, —OCF$_3$, —OH, $C_1$-$C_6$ alkoxy, hydroxyalkyl, —CN, —CO$_2$H, —SH, —S-alkyl, —SOR'R", —SO$_2$R', —NO$_2$, or NR'R", wherein R' and R" are independently H or ($C_1$-$C_6$) alkyl, and wherein each alkyl portion of a substituent is optionally further substituted with 1, 2, or 3 groups independently selected from halogen, CN, OH, and NH$_2$; and
$R_4$ and $R_5$ are independently H or alkyl, provided that when $R_3$ and $R_4$ are on the same carbon and $R_3$ is oxo, then $R_4$ is absent.

Aryladamantane compounds of Formula 7 include compounds of formula I-1:

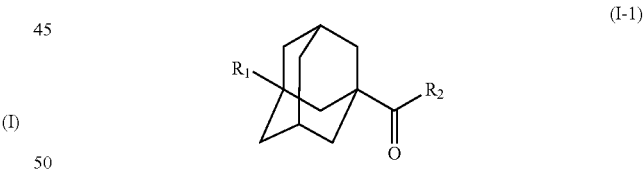

(I-1)

and pharmaceutically acceptable salts thereof, wherein:
$R_1$ is H, alkyl, cycloalkyl, cycloalkylalkyl, alkenyl, alkynyl, heteroalkyl, aryl, alkylaryl, alkenylaryl, heterocyclyl, heteroaryl, alkylheteroaryl, heterocycloalkyl, alkyl-heterocycloalkyl, acyl, aroyl, halogen, haloalkyl, alkoxy, haloalkoxy, hydroxyalkyl, alkanoyl, —COOH, —OH, —SH, —S-alkyl, —CN, —NO$_2$, —NH$_2$, —CO$_2$(alkyl), —OC(O)alkyl, carbamoyl, mono or dialkylaminocarbamoyl, mono or dialkylcarbamoyl, mono or dialkylamino, aminoalkyl, mono- or dialkylaminoalkyl, thiocarbamoyl, or mono or dialkylthiocarbamoyl; and
$R_2$ is H, alkyl, cycloalkyl, cycloalkylalkyl, alkenyl, alkynyl, heteroalkyl, aryl, alkylaryl, alkenylaryl, heterocyclyl, heteroaryl, alkylheteroaryl, heterocycloalkyl, alkyl-heterocycloalkyl, acyl, aroyl, halogen, haloalkyl, alkoxy, haloalkoxy, hydroxyalkyl, alkanoyl, —COOH, —OH, —SH, —S-alkyl, —CN, —NO$_2$, —NH$_2$, —CO$_2$(alkyl), —OC(O)alkyl, carbamoyl, mono or dialkylaminocarbamoyl, mono or dialkylcarbamoyl, mono or dialkylamino, aminoalkyl, mono- or dialkylaminoalkyl, thiocarbamoyl, mono or dialkylthiocarbamoyl, alkyl-S-alkyl, -heteroaryl-aryl, -alkyl-heteroaryl-aryl, —NH-aryl, -alkenyl-heteroaryl, -heteroaryl, —NH-alkyl, —NH— cycloalkyl, or -alkenyl-heteroaryl-aryl,
wherein the alkyl and ring portion of each of the above R$_1$, and R$_2$ groups is optionally substituted with up to 5 groups that are independently (C$_1$-C$_6$) alkyl, halogen, haloalkyl, —OC(O)(C$_1$-C$_6$ alkyl), —C(O)O(C$_1$-C$_6$ alkyl), —CONR'R", —OC(O)NR'R", —NR'C(O)R", —CF$_3$, —OCF$_3$, —OH, C$_1$-C$_6$ alkoxy, hydroxyalkyl, —CN, —CO$_2$H, —SH, —S-alkyl, —SOR'R", —SO$_2$R', —NO$_2$, or NR'R", wherein R' and R" are independently H or (C$_1$-C$_6$) alkyl, and wherein each alkyl portion of a substituent is optionally further substituted with 1, 2, or 3 groups independently selected from halogen, CN, OH, NH$_2$.

Aryladamantane compounds of Formula 7 include those of formula II:

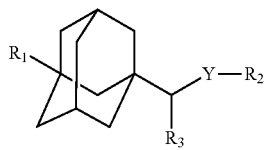

(II)

and pharmaceutically acceptable salts thereof, wherein:
Y is —C(R$_4$,R$_5$)—, —N(R$_4$)—, —O—, or —C(O)—;
R$_1$ is H, alkyl, cycloalkyl, cycloalkylalkyl, alkenyl, alkynyl, heteroalkyl, aryl, alkylaryl, alkenylaryl, heterocyclyl, heteroaryl, alkylheteroaryl, heterocycloalkyl, alkyl-heterocycloalkyl, acyl, aroyl, halogen, haloalkyl, alkoxy, haloalkoxy, hydroxyalkyl, alkanoyl, —COOH, —OH, —SH, —S-alkyl, —CN, —NO$_2$, —NH$_2$, —CO$_2$(alkyl), —OC(O)alkyl, carbamoyl, mono or dialkylaminocarbamoyl, mono or dialkylcarbamoyl, mono or dialkylamino, aminoalkyl, mono- or dialkylaminoalkyl, thiocarbamoyl, or mono or dialkylthiocarbamoyl;
R$_2$ is H, alkyl, cycloalkyl, cycloalkylalkyl, alkenyl, alkynyl, heteroalkyl, aryl, alkylaryl, alkenylaryl, heterocyclyl, heteroaryl, alkylheteroaryl, heterocycloalkyl, alkyl-heterocycloalkyl, acyl, aroyl, halogen, haloalkyl, alkoxy, haloalkoxy, hydroxyalkyl, alkanoyl, —COOH, —OH, —SH, —S-alkyl, —CN, —NO$_2$, —NH$_2$, —CO$_2$(alkyl), —OC(O)alkyl, carbamoyl, mono or dialkylaminocarbamoyl, mono or dialkylcarbamoyl, mono or dialkylamino, aminoalkyl, mono- or dialkylaminoalkyl, thiocarbamoyl, mono or dialkylthiocarbamoyl, alkyl-S-alkyl, -heteroaryl-aryl, -alkyl-heteroaryl-aryl, —C(O)—NH-aryl, -alkenyl-heteroaryl, —C(O)-heteroaryl, or -alkenyl-heteroaryl-aryl;
R$_3$ is H, alkyl, cycloalkyl, cycloalkylalkyl, alkenyl, alkynyl, heteroalkyl, aryl, alkylaryl, alkenylaryl, heterocyclyl, heteroaryl, alkylheteroaryl, heterocycloalkyl, alkyl-heterocycloalkyl, acyl, aroyl, halogen, haloalkyl, alkoxy, haloalkoxy, hydroxyalkyl, alkanoyl, oxo (=O), —COOH, —OH, —SH, —S-alkyl, —CN, —NO$_2$, —NH$_2$, —CO$_2$(alkyl), —OC(O)alkyl, carbamoyl, mono or dialkylaminocarbamoyl, mono or dialkylcarbamoyl, mono or dialkylamino, aminoalkyl, mono- or dialkylaminoalkyl, thiocarbamoyl, or mono or dialkylthiocarbamoyl;
wherein the alkyl and ring portion of each of the above R$_1$, R$_2$, and R$_3$ groups is optionally substituted with up to 5 groups that are independently (C$_1$-C$_6$) alkyl, halogen, haloalkyl, —OC(O)(C$_1$-C$_6$ alkyl), —C(O)O(C$_1$-C$_6$ alkyl), —CONR'R", —OC(O)NR'R", —NR'C(O)R", —CF$_3$, —OCF$_3$, —OH, C$_1$-C$_6$ alkoxy, hydroxyalkyl, —CN, —CO$_2$H, —SH, —S-alkyl, —SOR'R", —SO$_2$R', —NO$_2$, or NR'R", wherein R' and R" are independently H or (C$_1$-C$_6$) alkyl, and wherein each alkyl portion of a substituent is optionally further substituted with 1, 2, or 3 groups independently selected from halogen, CN, OH, NH$_2$; and
R$_4$ and R$_5$ are independently H or alkyl.

Compounds of the formula II include those wherein:
Y is —C(R$_4$,R$_5$)— or —N(R$_4$)—;
R$_1$ is H, alkyl, cycloalkyl, cycloalkylalkyl, alkenyl, alkynyl, heteroalkyl, aryl, alkylaryl, alkenylaryl, heterocyclyl, heteroaryl, alkylheteroaryl, heterocycloalkyl, alkyl-heterocycloalkyl, acyl, aroyl, halogen, haloalkyl, alkoxy, haloalkoxy, hydroxyalkyl, alkanoyl, —COOH, —OH, —SH, —S-alkyl, —CN, —NO$_2$, —NH$_2$, —CO$_2$(alkyl), —OC(O)alkyl, carbamoyl, mono or dialkylaminocarbamoyl, mono or dialkylcarbamoyl, mono or dialkylamino, aminoalkyl, mono- or dialkylaminoalkyl, thiocarbamoyl, or mono or dialkylthiocarbamoyl;
R$_2$ is H, alkyl, cycloalkyl, cycloalkylalkyl, alkenyl, alkynyl, heteroalkyl, aryl, alkylaryl, alkenylaryl, heterocyclyl, heteroaryl, alkylheteroaryl, heterocycloalkyl, alkyl-heterocycloalkyl, acyl, aroyl, halogen, haloalkyl, alkoxy, haloalkoxy, hydroxyalkyl, alkanoyl, —COOH, —OH, —SH, —S-alkyl, —CN, —NO$_2$, —NH$_2$, —CO$_2$(alkyl), —OC(O)alkyl, carbamoyl, mono or dialkylaminocarbamoyl, mono or dialkylcarbamoyl, mono or dialkylamino, aminoalkyl, mono- or dialkylaminoalkyl, thiocarbamoyl, mono or dialkylthiocarbamoyl, alkyl-S-alkyl, -heteroaryl-aryl, -alkyl-heteroaryl-aryl, —C(O)—NH-aryl, -alkenyl-heteroaryl, —C(O)-heteroaryl, or -alkenyl-heteroaryl-aryl;
wherein the alkyl and ring portion of each of the above R$_1$ and R$_2$ groups is optionally substituted with up to 5 groups that are independently (C$_1$-C$_6$) alkyl, halogen, haloalkyl, —OC(O)(C$_1$-C$_6$ alkyl), —C(O)O(C$_1$-C$_6$ alkyl), —CONR$_4$R$_5$, —OC(O)NR$_4$R$_5$, —NR$_4$C(O)R$_5$, —CF$_3$, —OCF$_3$, —OH, C$_1$-C$_6$ alkoxy, hydroxyalkyl, —CN, —CO$_2$H, —SH, —S-alkyl, —SOR$_4$R$_5$, —SO$_2$R$_4$R$_5$, —NO$_2$, or NR$_4$R$_5$, and wherein each alkyl portion of a substituent is optionally further substituted with 1, 2, or 3 groups independently selected from halogen, CN, OH, NH$_2$;
R$_3$ is H, alkyl, or oxo (=O); and
R$_4$ and R$_5$ are independently H or (C$_1$-C$_6$)alkyl.
Representative formula II compounds include:

| Cmpd | Chemical name | Y | R3 | R1 | R2 |
|---|---|---|---|---|---|
| 1 | 3-(4-Chloro-phenyl)-adamantane-1-carboxylic acidisopropylamide | NH | =O | Cl—⟨phenyl⟩— | —CH(CH$_3$)$_2$ |

-continued

| Cmpd | Chemical name | Y | R3 | R1 | R2 |
|---|---|---|---|---|---|
| 2 | 3-(4-Chloro-phenyl)-adamantane-1-carboxylic acidcyclopropylamide | NH | =O | 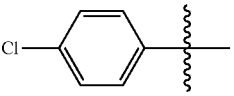 | 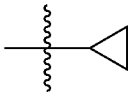 [SMILES: *C1CC1] |
| 3 | 3-(4-Chloro-phenyl)-adamantane-1-carboxylic acid(2-ethylsulfanyl-ethyl)-amide | NH | =O | 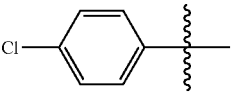 | 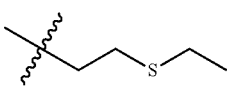 [SMILES: *CCSCC] |
| 4 | 3-(4-Chloro-phenyl)-adamantane-1-carboxylic acidphenylamide | NH | =O | 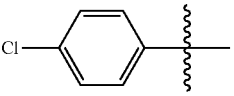 | 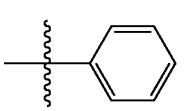 [SMILES: *c1ccccc1] |
| 5 | Adamantane-1-carboxylic acid(4-hydroxy-phenyl)-amide | NH | =O | H | 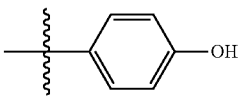 [SMILES: *c1ccc(O)cc1] |
| 6 | 3-(4-Chloro-phenyl)-adamantane-1-carboxylic acid(4-hydroxy-phenyl)-amide | NH | =O | 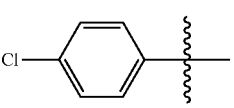 | 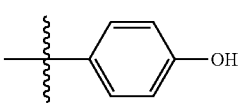 |
| 7 | Acetic acid 4-{[3-(4-chloro-phenyl)-adamantane-1-carbonyl]-amino}-phenyl ester | NH | =O | 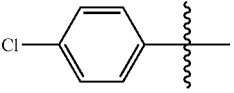 | 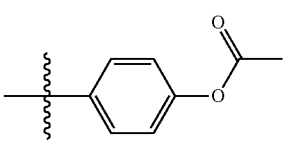 [SMILES: *c1ccc(OC(C)=O)cc1] |
| 8 | 3-(4-Chloro-phenyl)-adamantane-1-carboxylic acid(2,4-dihydroxy-phenyl)-amide | NH | =O | 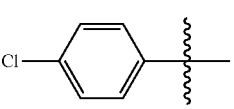 | 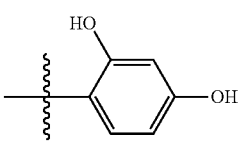 [SMILES: *c1ccc(O)cc1O] |
| 9 | 3-(4-Chloro-phenyl)-adamantane-1-carboxylic acid(3-hydroxymethyl-phenyl)-amide | NH | =O | 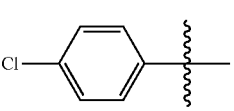 | 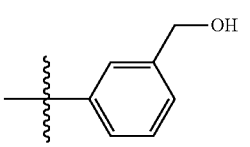 [SMILES: *c1cccc(CO)c1] |
| 10 | Adamantane-1-carboxylic acid(4-cyanomethyl-phenyl)-amide | NH | =O | H | 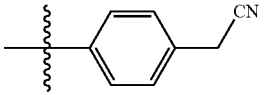 |
| 11 | 3-(4-Chloro-phenyl)-adamantane-1-carboxylic acid(4-cyanomethyl-phenyl)-amide | NH | =O | 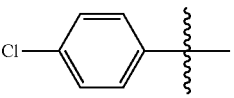 | 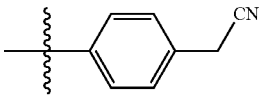 [SMILES: *c1ccc(CC#N)cc1] |
| 12 | 3-(4-Chloro-phenyl)-adamantane-1-carboxylic acidbenzylamide | NH | =O | 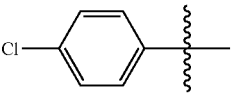 [SMILES: *c1ccc(Cl)cc1] | 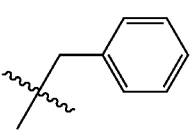 [SMILES: *Cc1ccccc1] |
| 13 | 3-(4-Chloro-phenyl)-adamantane-1-carboxylic acid4-tert-butyl-benzylamide | NH | =O | 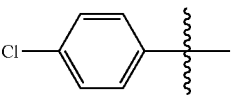 | 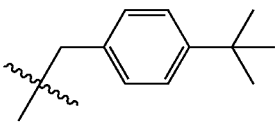 [SMILES: *Cc1ccc(C(C)(C)C)cc1] |

-continued

| Cmpd | Chemical name | Y | R3 | R1 | R2 |
|---|---|---|---|---|---|
| 14 | 3-(4-Chloro-phenyl)-adamantane-1-carboxylic acid4-methylsulfanyl-benzylamide | NH | =O | 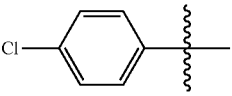 | 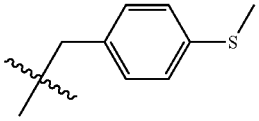 [SMILES: *Cc1ccc(SC)cc1] |
| 15 | 3-(4-Chloro-phenyl)-adamantane-1-carboxylic acid3-trifluoromethyl-benzylamide | NH | =O | 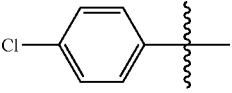 | 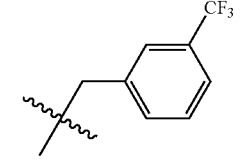 [SMILES: *Cc1cccc(C(F)(F)F)c1] |
| 16 | 3-(4-Chloro-phenyl)-adamantane-1-carboxylic acid4-trifluoromethyl-benzylamide | NH | =O | 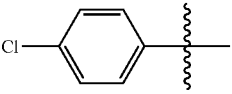 | 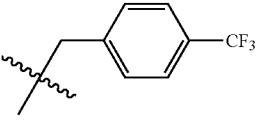 [SMILES: *Cc1ccc(C(F)(F)F)cc1] |
| 17 | 3-(4-Chloro-phenyl)-adamantane-1-carboxylic acid3,5-bis-trifluoromethyl-benzylamide | NH | =O | 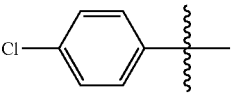 | 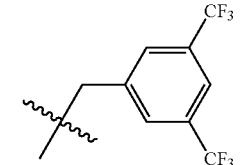 [SMILES: *Cc1cc(F)cc(C(F)(F)F)c1] |
| 18 | 3-(4-Chloro-phenyl)-adamantane-1-carboxylic acid3-fluoro-5-trifluoromethyl-benzylamide | NH | =O | 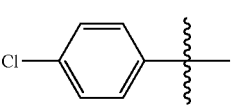 | 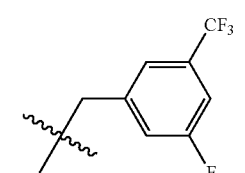 |
| 19 | 3-(4-Chloro-phenyl)-adamantane-1-carboxylic acid2-fluoro-4-trifluoromethyl-benzylamide | NH | =O | 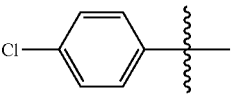 [SMILES: *c1ccc(Cl)cc1] | 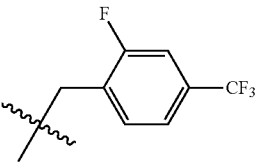 [SMILES: *Cc1ccc(C(F)(F)F)cc1F] |
| 20 | 3-(4-Chloro-phenyl)-adamantane-1-carboxylic acid3,5-difluoro-benzylamide | NH | =O | 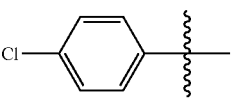 [SMILES: *c1ccc(Cl)cc1] | 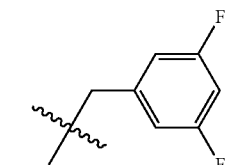 |
| 21 | 3-(4-Chloro-phenyl)-adamantane-1-carboxylic acid3,4-difluoro-benzylamide | NH | =O | 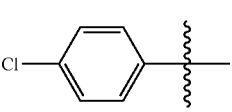 | 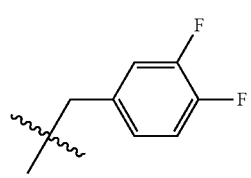 |
| 22 | 3-(4-Chloro-phenyl)-adamantane-1-carboxylic acid3,4,5-trifluoro-benzylamide | NH | =O | 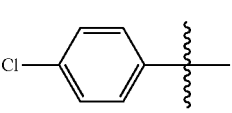 [SMILES: *c1ccc(Cl)cc1] | 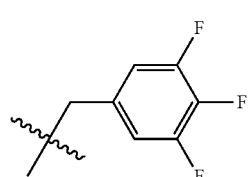 [SMILES: *Cc1ccc(F)c(F)c1] |

-continued

| Cmpd | Chemical name | Y | R3 | R1 | R2 |
|------|---------------|---|-----|-----|-----|
| 23 | 3-(4-Chloro-phenyl)-adamantane-1-carboxylic acid3-chloro-4-fluoro-benzylamide | NH | =O | 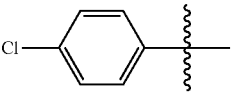 | 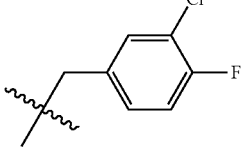 |
| 24 | 3-(4-Chloro-phenyl)-adamantane-1-carboxylic acid4-fluoro-3-trifluoromethyl-benzylamide | NH | =O | 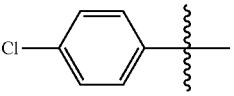 [SMILES: *c1ccc(Cl)cc1] | 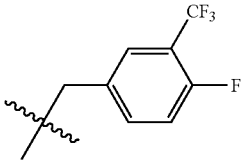 [SMILES: *Cc1ccc(F)c(Cl)c1] |
| 25 | 3-(4-Chloro-phenyl)-adamantane-1-carboxylic acid2-chloro-4-fluoro-benzylamide | NH | =O | 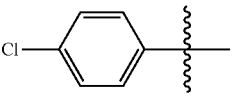 | 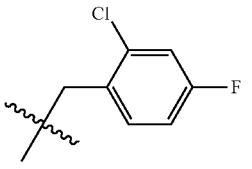 [SMILES: *Cc1ccc(F)cc1Cl] |
| 26 | 3-(4-Chloro-phenyl)-adamantane-1-carboxylic acid4-chloro-3-trifluoromethyl-benzylamide | NH | =O | 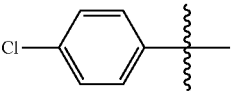 | 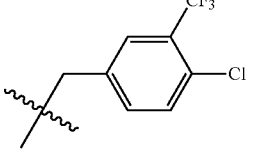 |
| 27 | 3-(4-Chloro-phenyl)-adamantane-1-carboxylic acid3-aminomethyl-2,4,5,6-tetrachloro-benzylamide | NH | =O | 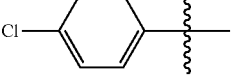 | 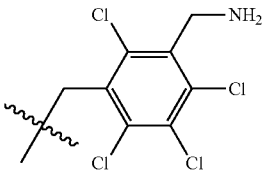 [SMILES: *Cc1c(Cl)c(Cl)c(Cl)c(CN)c1Cl] |
| 28 | 3-(4-Chloro-phenyl)-adamantane-1-carboxylic acid[1-(4-chloro-phenyl)-ethyl]-amide | NH | =O | 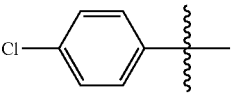 | 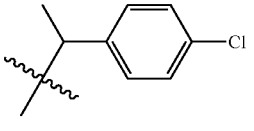 [SMILES: *C(C)c1ccc(Cl)cc1] |
| 29 | 3-(4-Chloro-phenyl)-adamantane-1-carboxylic acid[1-(4-bromo-phenyl)-ethyl]-amide | NH | =O | 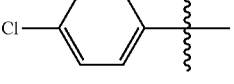 | 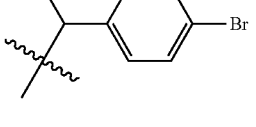 |
| 30 | 3-(4-Chloro-phenyl)-adamantane-1-carboxylic acid4-methanesulfonyl-benzylamide | NH | =O | 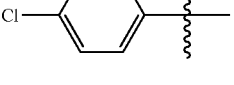 | 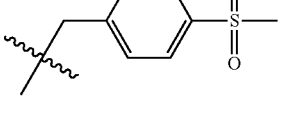 |
| 31 | 3-(4-Chloro-phenyl)-adamantane-1-carboxylic acid4-dimethylamino-benzylamide | NH | =O | 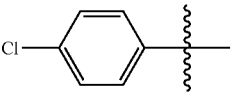 | 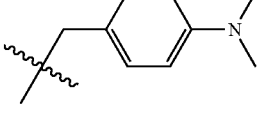 |
| 32 | 3-(4-Chloro-phenyl)-adamantane-1-carboxylic acid4-trifluoromethoxy-benzylamide | NH | =O | 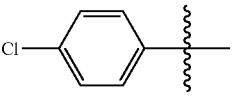 | 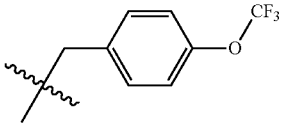 |

| Cmpd | Chemical name | Y | R3 | R1 | R2 |
|---|---|---|---|---|---|
| 33 | 3-(4-Chloro-phenyl)-adamantane-1-carboxylic acid3-trifluoromethoxy-benzylamide | NH | =O | 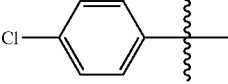 | 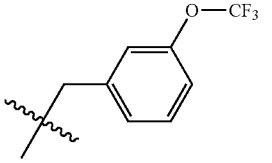 [SMILES: *Cc1cccc(OC(F)(F)F)c1] |
| 34 | 3-(4-Chloro-phenyl)-adamantane-1-carboxylic acid4-phenoxy-benzylamide | NH | =O | 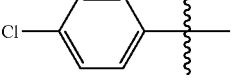 | 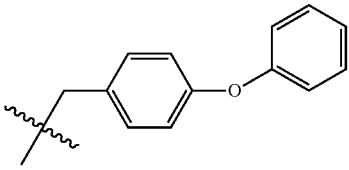 [SMILES: *Cc1ccc(Oc2ccccc2)cc1] |
| 35 | Adamantane-1-carboxylic acid3,4-dihydroxy-benzylamide | NH | =O | H | 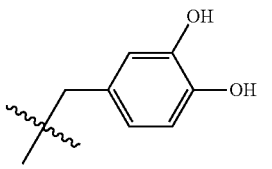 [SMILES: *Cc1ccc(O)c(O)c1] |
| 36 | 3-(4-Chloro-phenyl)-adamantane-1-carboxylic acid3,4-dihydroxy-benzylamide | NH | =O | 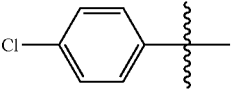 | 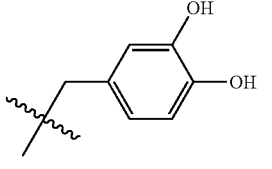 [SMILES: *Cc1ccc(O)c(O)c1] |
| 37 | 3-(4-Chloro-phenyl)-adamantane-1-carboxylic acidphenethyl-amide | NH | =O | 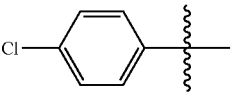 [SMILES: *c1ccc(Cl)cc1] | 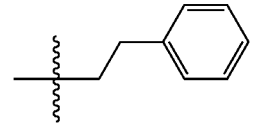 [SMILES: *CCc1ccccc1] |
| 38 | 3-(4-Chloro-phenyl)-adamantane-1-carboxylic acid[2-(4-fluoro-phenyl)-ethyl]-amide | NH | =O | 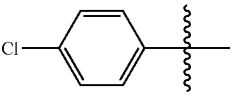 | 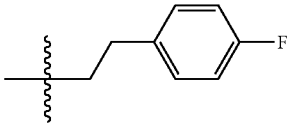 [SMILES: *CCc1ccc(F)cc1] |
| 39 | 3-(4-Chloro-phenyl)-adamantane-1-carboxylic acid[2-(4-bromo-phenyl)-ethyl]-amide | NH | =O | 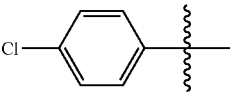 | 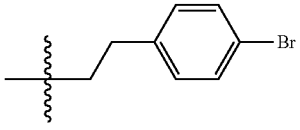 |
| 40 | 3-(4-Chloro-phenyl)-adamantane-1-carboxylic acid[2-(4-hydroxy-phenyl)-ethyl]-amide | NH | =O | 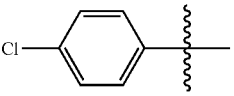 | 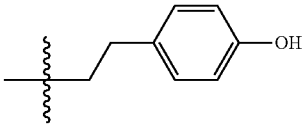 [SMILES: *CCc1ccc(O)cc1] |
| 41 | 3-(4-Chloro-phenyl)-adamantane-1-carboxylic acid4-phenoxy-benzylamide | NH | =O | 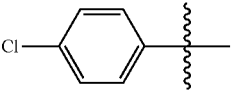 | 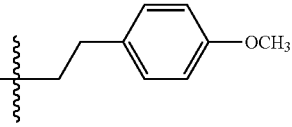 |
| 42 | 3-(4-Chloro-phenyl)-adamantane-1-carboxylic acid[2-(3-bromo-4-methoxy-phenyl)-ethyl]-amide | NH | =O | 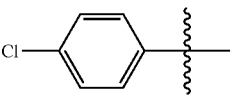 | 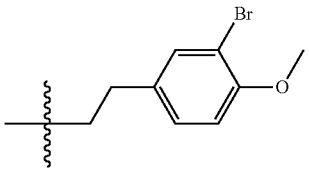 [SMILES: *CCc1ccc(OC)c(Br)c1] |

| Cmpd | Chemical name | Y | R3 | R1 | R2 |
|---|---|---|---|---|---|
| 43 | Adamantane-1-carboxylic acid[2-(3,4-dihydroxy-phenyl)-ethyl]-amide | NH | =O | H | 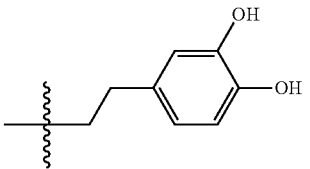 [SMILES: *CCc1ccc(O)c(O)c1] |
| 44 | 3-(4-Chloro-phenyl)-adamantane-1-carboxylic acid[2-(3,4-dihydroxy-phenyl)-ethyl]-amide | NH | =O | 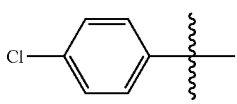 | 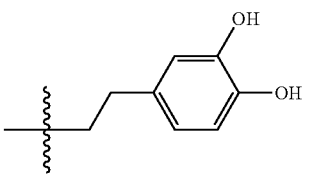 [SMILES: *CCc1ccc(O)c(O)c1] |
| 45 | 3-(4-Chloro-phenyl)-adamantane-1-carboxylic acid(2-benzo[1,3]dioxol-5-yl-ethyl)-amide | NH | =O | 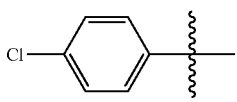 | 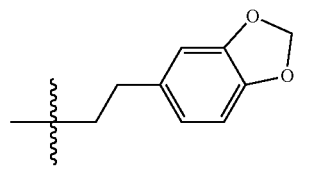 [SMILES: *CCc1ccc2c(c1)OCO2] |
| 46 | 3-(4-Chloro-phenyl)-adamantane-1-carboxylic acid[2-(3-phenoxy-phenyl)-ethyl]-amide | NH | =O | 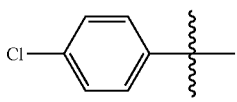 | 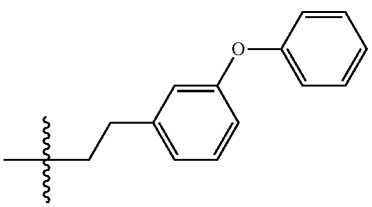 [SMILES: *CCc1cccc(Oc2ccccc2)c1] |
| 47 | 3-(4-Chloro-phenyl)-adamantane-1-carboxylic acid[2-(4-phenoxy-phenyl)-ethyl]-amide | NH | =O | 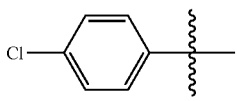 [SMILES: *c1ccc(Cl)cc1] | 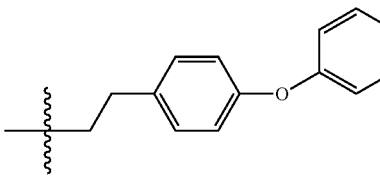 |
| 48 | 3-(4-Chloro-phenyl)-adamantane-1-carboxylic acid(3-phenyl-propyl)-amide | NH | =O | 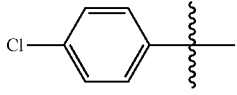 [SMILES: *c1ccc(Cl)cc1] | 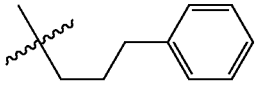 [SMILES: *CCCc1ccccc1] |
| 49 | 3-(4-Chloro-phenyl)-adamantane-1-carboxylic acid(biphenyl-4-ylmethyl)-amide | NH | =O | 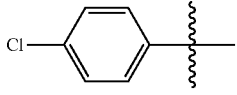 | 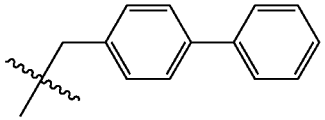 [SMILES: *Cc1ccc(-c2ccccc2)cc1] |
| 50 | Adamantane-1-carboxylic acid(1-methyl-piperidin-4-yl)-amide | NH | =O | H | 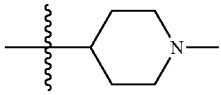 |
| 51 | 3-(4-Chloro-phenyl)-adamantane-1-carboxylic acid(1-methyl-piperidin-4-yl)-amide | NH | =O | 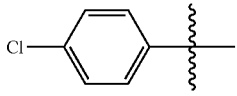 | 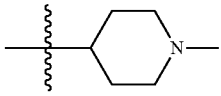 [SMILES: *C1CCN(C)CC1] |
| 52 | 3-(4-Chloro-phenyl)-adamantane-1-carboxylic acid(4-methyl-piperazin-1-yl)-amide | NH | =O | 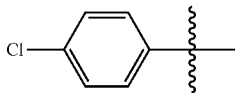 [SMILES: *c1ccc(Cl)cc1] | 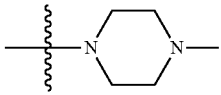 |

-continued

| Cmpd | Chemical name | Y | R3 | R1 | R2 |
|---|---|---|---|---|---|
| 53 | 3-(4-Chloro-phenyl)-adamantane-1-carboxylic acid(3-tert-butylamino-propyl)-amide | NH | =O | 4-Cl-C6H4- | -(CH2)3-NH-C(CH3)3 |
| 54 | 3-(4-Chloro-phenyl)-adamantane-1-carboxylic acid(3-pyrrolidin-1-yl-propyl)-amide | NH | =O | 4-Cl-C6H4- | -(CH2)3-pyrrolidin-1-yl |
| 55 | 3-(4-Chloro-phenyl)-adamantane-1-carboxylic acid[3-(2-oxo-pyrrolidin-1-yl)-propyl]-amide | NH | =O | 4-Cl-C6H4- | -(CH2)3-(2-oxo-pyrrolidin-1-yl) |
| 56 | Adamantane-1-carboxylic acid[2-(1-methyl-pyrrolidin-2-yl)-ethyl]-amide | NH | =O | H | -(CH2)2-(1-methyl-pyrrolidin-2-yl) |
| 57 | 3-(4-Chloro-phenyl)-adamantane-1-carboxylic acid[2-(1-methyl-pyrrolidin-2-yl)-ethyl]-amide | NH | =O | 4-Cl-C6H4- | -(CH2)2-(1-methyl-pyrrolidin-2-yl) |
| 58 | 3-(4-Chloro-phenyl)-adamantane-1-carboxylic acid(2-morpholin-4-yl-ethyl)-amide | NH | =O | 4-Cl-C6H4- | -(CH2)2-morpholin-4-yl |
| 59 | 3-(4-Chloro-phenyl)-adamantane-1-carboxylic acid(2-piperazin-1-yl-ethyl)amide | NH | =O | 4-Cl-C6H4- | -(CH2)2-piperazin-1-yl |
| 60 | Adamantane-1-carboxylic acid(pyridin-4-ylmethyl)-amide | NH | =O | H | -CH2-pyridin-4-yl |
| 61 | 3-(4-Fluoro-phenyl)-adamantane-1-carboxylic acid(pyridin-4-ylmethyl)-amide | NH | =O | 4-F-C6H4- | -CH2-pyridin-4-yl |
| 62 | 3-(4-Chloro-phenyl)-adamantane-1-carboxylic acid(pyridin-4-ylmethyl)-amide | NH | =O | 4-Cl-C6H4- | -CH2-pyridin-4-yl |
| 63 | Adamantane-1-carboxylic acid(pyridin-4-ylmethyl)-amide | NH | =O | H | -(CH2)2-pyridin-4-yl |

-continued

| Cmpd | Chemical name | Y | R3 | R1 | R2 |
|---|---|---|---|---|---|
| 64 | 3-(4-Chloro-phenyl)-adamantane-1-carboxylic acid(2-pyridin-4-yl-ethyl)-amide | NH | =O | 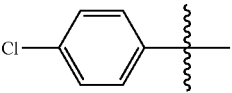 | 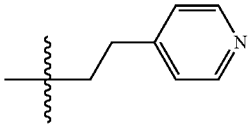 |
| 65 | 3-(4-Chloro-phenyl)-adamantane-1-carboxylic acid(3-imidazol-1-yl-propyl)-amide | NH | =O | 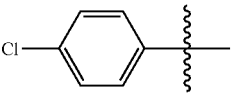 [SMILES: *c1ccc(Cl)cc1] | 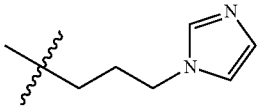 [SMILES: *CCCn1ccnc1] |
| 66 | 3-(4-Chloro-phenyl)-adamantane-1-carboxylic acid(2-methyl-1H-indol-5-yl)-amide | NH | =O | 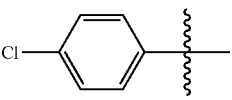 | 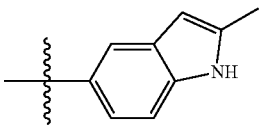 |
| 67 | 3-(4-Chloro-phenyl)-adamantane-1-carboxylic acid(1H-tetrazol-5-yl)-amide | NH | =O | 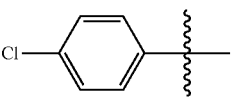 | 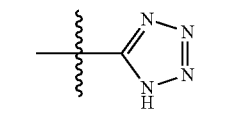 |
| 68 | 3-(4-Chloro-phenyl)-adamantane-1-carboxylic acid(9-ethyl-9H-carbazol-3-yl)-amide | NH | =O | 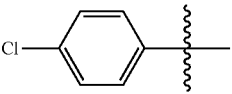 | 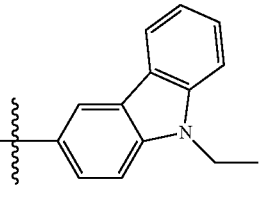 |
| 69 | Adamantane-1-carboxylic acid[4-(4-chloro-phenyl)-thiazol-2-yl]-amide | NH | =O | H | 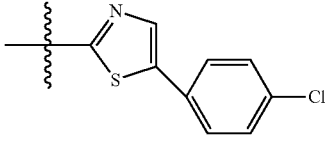 [SMILES: *c1ncc(-c2ccc(Cl)cc2)s1] |
| 70 | 3-(4-Chloro-phenyl)-adamantane-1-carboxylic acid[4-(4-chloro-phenyl)-thiazol-2-yl]-amide | NH | =O | 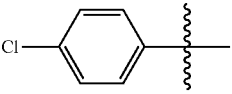 | 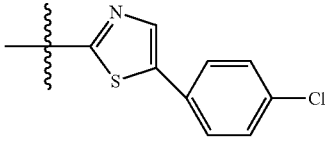 [SMILES: *c1ncc(-c2ccc(Cl)cc2)s1] |
| 71 | 3-(4-Chloro-phenyl)-adamantane-1-carboxylic acidbenzothiazol-2-ylamide | NH | =O | 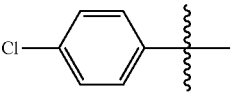 [SMILES: *c1ccc(Cl)cc1] | 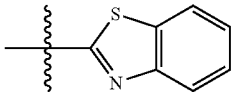 [SMILES: *c1nc2ccccc2s1] |
| 72 | 3-(4-Chloro-phenyl)-adamantane-1-carboxylic acid(5-chloro-benzooxazol-2-yl)-amide | NH | =O | 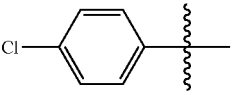 | 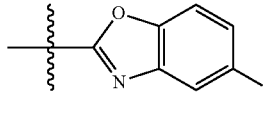 |
| 73 | 3-(4-Chloro-phenyl)-adamantane-1-carboxylic acid(9H-purin-6-yl)-amide | NH | =O | 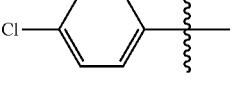 | 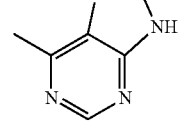 |
| 75 | [3-(4-Chloro-phenyl)-adamantan-1-ylmethyl]-isopropyl-amine | NH | H | 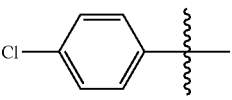 | 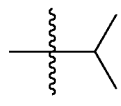 [SMILES: *C(C)C] |

-continued

| Cmpd | Chemical name | Y | R3 | R1 | R2 |
|---|---|---|---|---|---|
| 76 | 4- and -phenol | NH | H | 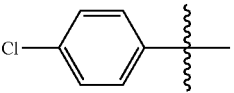 | 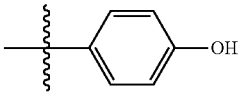 |
| 77 | [3-(4-Chloro-phenyl)-adamantan-1-ylmethyl]-(4-trifluoromethyl-benzyl)-amine | NH | H | 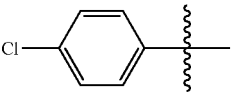 | 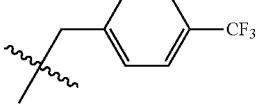 |
| 78 | [3-(4-Chloro-phenyl)-adamantan-1-ylmethyl]-(2-fluoro-4-trifluoromethyl-benzyl)-amine | NH | H | 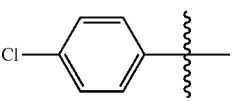 [SMILES: *c1ccc(Cl)cc1] | 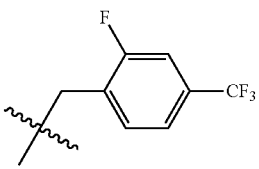 |
| 79 | [3-(4-Chloro-phenyl)-adamantan-1-ylmethyl]-(4-fluoro-3-trifluoromethyl-benzyl)-amine | NH | H | 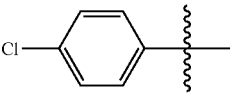 [SMILES: *c1ccc(Cl)cc1] | 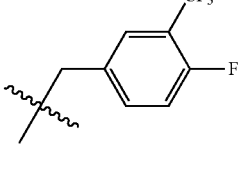 |
| 80 | [3-(4-Chloro-phenyl)-adamantan-1-ylmethyl]-(4-trifluoromethoxy-benzyl)-amine | NH | H | 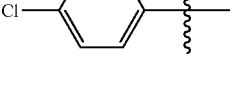 | 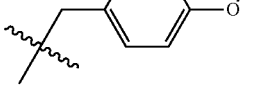 |
| 81 | [3-(4-Chloro-phenyl)-adamantan-1-ylmethyl]-[2-(3-phenoxy-phenyl)-ethyl]-amine | NH | H | 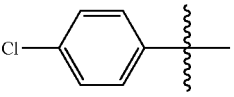 | 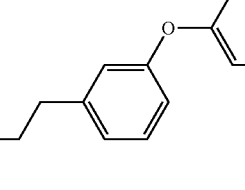 |
| 82 | [3-(4-Chloro-phenyl)-adamantan-1-ylmethyl]-(1-methyl-piperidin-4-yl)-amine | NH | H | 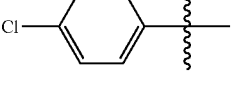 | 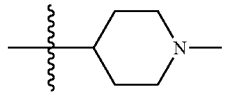 [SMILES: *C1CCN(C)CC1] |
| 83 | [3-(4-Chloro-phenyl)-adamantan-1-ylmethyl]-(4-methyl-piperazin-1-yl)-amine | NH | H | 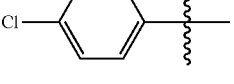 | 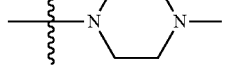 |
| 84 | N-tert-Butyl-N'-[3-(4-chloro-phenyl)-adamantan-1-ylmethyl]-propane-1,3-diamine | NH | H | 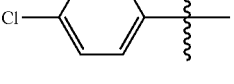 | 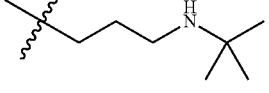 |
| 85 | [3-(4-Chloro-phenyl)-adamantan-1-ylmethyl]-(3-pyrrolidin-1-yl-propyl)-amine | NH | H | 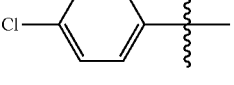 | 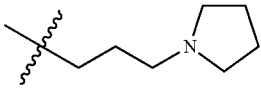 [SMILES: *CCCN1CCCC1] |
| 86 | [3-(4-Chloro-phenyl)-adamantan-1-ylmethyl]-[2-(1-methyl-pyrrolidin-2-yl)-ethyl]-amine | NH | H | 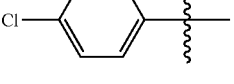 | 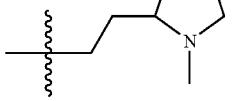 |

-continued

| Cmpd | Chemical name | Y | R3 | R1 | R2 |
|---|---|---|---|---|---|
| 87 | [3-(4-Chloro-phenyl)-adamantan-1-ylmethyl]-(2-morpholin-4-yl-ethyl)-amine | NH | H | 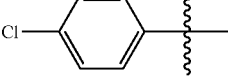 | 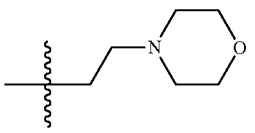 |
| 88 | [3-(4-Chloro-phenyl)-adamantan-1-ylmethyl]-pyridin-4-ylmethyl-amine | NH | H | 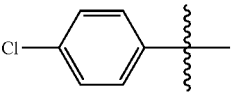 [SMILES: *c1ccc(Cl)cc1] | 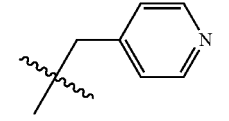 [SMILES: *Cc1ccncc1] |
| 89 | [3-(4-Chloro-phenyl)-adamantan-1-ylmethyl]-(9-ethyl-9H-carbazol-3-yl)-amine | NH | H | 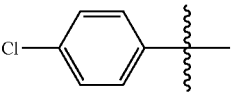 [SMILES: *c1ccc(Cl)cc1] | 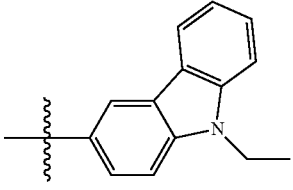 [SMILES: *c1ccc2c(c1)c1ccccc1n2CC] |
| 90 | [3-(4-Chloro-phenyl)-adamantan-1-ylmethyl]-[5-(4-chloro-phenyl)-thiazol-2-yl]-amine | NH | H | 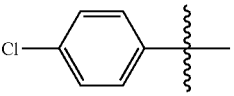 [SMILES: *c1ccc(Cl)cc1] | 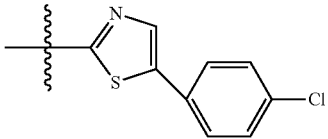 [SMILES: *c1ncc(-c2ccc(Cl)cc2)s1] |
| 91 | 1-[3-(4-Chloro-phenyl)-adamantan-1-yl]-ethylamine | NH | CH3 | 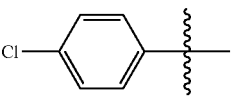 | H |
| 92 | {1-[3-(4-Chloro-phenyl)-adamantan-1-yl]-ethyl}-isopropyl-amine | NH | CH3 | 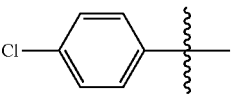 [SMILES: *c1ccc(Cl)cc1] | 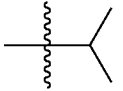 [SMILES: *C(C)C] |
| 93 | Phenyl-[1-(3-phenyl-adamantan-1-yl)-ethyl]-amine | NH | CH3 | 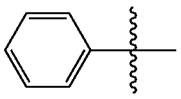 [SMILES: *c1ccccc1] | 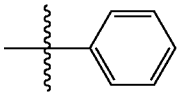 [SMILES: *c1ccccc1] |
| 94 | {1-[3-(4-Fluoro-phenyl)-adamantan-1-yl]-ethyl}-phenyl-amine | NH | CH3 | 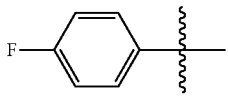 [SMILES: *c1ccc(F)cc1] | 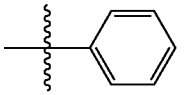 [SMILES: *c1ccccc1] |
| 95 | {1-[3-(4-Chloro-phenyl)-adamantan-1-yl]-ethyl}-phenyl-amine | NH | CH3 | 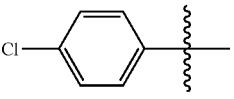 [SMILES: *c1ccc(Cl)cc1] | 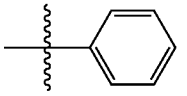 [SMILES: *c1ccccc1] |
| 96 | (1-Adamantan-1-yl-ethyl)-benzyl-amine | NH | CH3 | H | 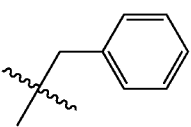 [SMILES: *Cc1ccccc1] |
| 97 | Benzyl-[1-(3-phenyl-adamantan-1-yl)-ethyl]-amine | NH | CH3 | 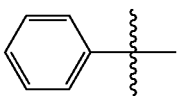 | 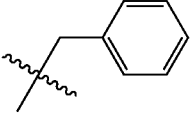 [SMILES: *Cc1ccccc1] |
| 98 | Benzyl-{1-[3-(4-fluoro-phenyl)-adamantan-1-yl]-ethyl}-amine | NH | CH3 | 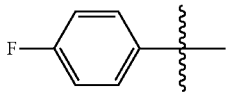 [SMILES: *c1ccc(F)cc1] | 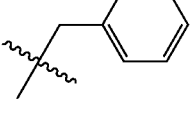 |

-continued

| Cmpd | Chemical name | Y | R3 | R1 | R2 |
|---|---|---|---|---|---|
| 99 | Benzyl-{1-[3-(4-chloro-phenyl)-adamantan-1-yl]-ethyl}-amine | NH | CH3 | 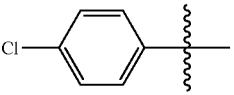 [SMILES: *c1ccc(Cl)cc1] | 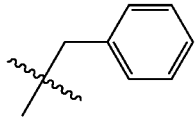 [SMILES: *Cc1ccccc1] |
| 100 | (4-tert-Butyl-benzyl)-{1-[3-(4-chloro-phenyl)-adamantan-1-yl]-ethyl}-amine | NH | CH3 | 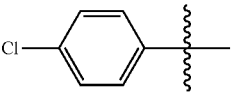 [SMILES: *c1ccc(Cl)cc1] | 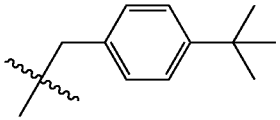 |
| 101 | [1-(4-Bromo-phenyl)-ethyl]-{1-[3-(4-chloro-phenyl)-adamantan-1-yl]-ethyl}-amine | NH | CH3 | 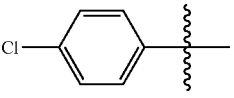 | 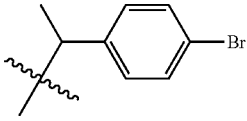 [SMILES: *C(C)c1ccc(Br)cc1] |
| 102 | (1-Adamantan-1-yl-ethyl)-[2-(4-bromo-phenyl)-ethyl]-amine | NH | CH3 | H | 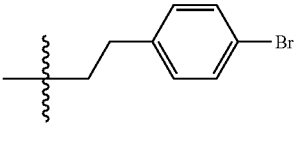 |
| 103 | [2-(4-Bromo-phenyl)-ethyl]-{1-[3-(4-chloro-phenyl)-adamantan-1-yl]-ethyl}-amine | NH | CH3 | 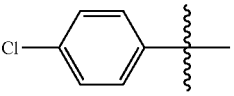 | 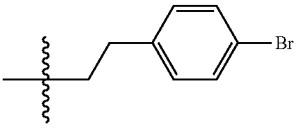 [SMILES: *CCc1ccc(Br)cc1] |
| 104 | (1-Adamantan-1-yl-ethyl)-(1-methyl-piperidin-4-yl)-amine | NH | CH3 | H | 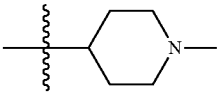 [SMILES: *C1CCN(C)CC1] |
| 105 | (1-Methyl-piperidin-4-yl)-[1-(3-phenyl-adamantan-1-yl)-ethyl]-amine | NH | CH3 | 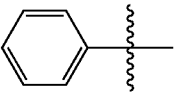 | 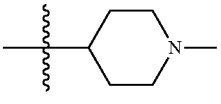 [SMILES: *C1CCN(C)CC1] |
| 106 | {1-[3-(4-Fluoro-phenyl)-adamantan-1-yl]-ethyl}-(1-methyl-piperidin-4-yl)-amine | NH | CH3 | 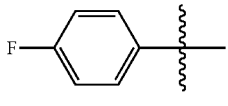 | 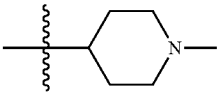 |
| 107 | {1-[3-(4-Chloro-phenyl)-adamantan-1-yl]-ethyl}-(1-methyl-piperidin-4-yl)-amine | NH | CH3 | 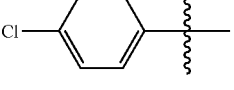 | 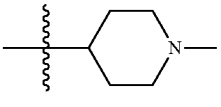 [SMILES: *C1CCN(C)CC1] |
| 108 | {1-[3-(4-Chloro-phenyl)-adamantan-1-yl]-ethyl}-(4-methyl-piperazin-1-yl)-amine | NH | CH3 | 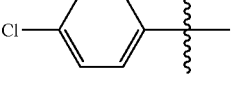 | 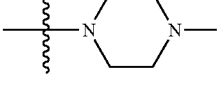 |
| 109 | {1-[3-(Phenyl)-adamantan-1-yl]-ethyl}-pyridin-4-ylmethyl-amine | NH | CH3 | 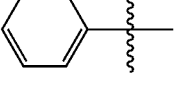 | 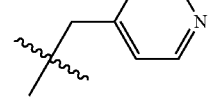 |
| 110 | {1-[3-(4-Chloro-phenyl)-adamantan-1-yl]-ethyl}-(6-chloro-pyridin-3-ylmethyl)-amine | NH | CH3 | 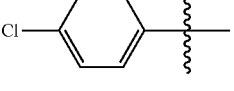 | 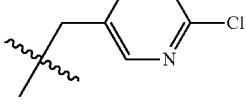 |

-continued

| Cmpd | Chemical name | Y | R3 | R1 | R2 |
|---|---|---|---|---|---|
| 111 | {1-[3-(4-Chloro-phenyl)-adamantan-1-yl]-ethyl}-(2-pyridin-4-yl-ethyl)-amine | NH | CH3 | 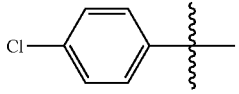 | 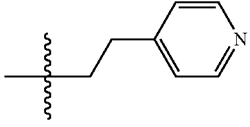 |
| 112 | {1-[3-(4-Chloro-phenyl)-adamantan-1-yl]-ethyl}-(3H-imidazol-4-ylmethyl)-amine | NH | CH3 | 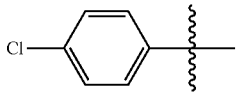 | 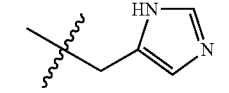 |
| 113 | {1-[3-(4-Chloro-phenyl)-adamantan-1-yl]-ethyl}-(2-methyl-1H-indol-5-yl)-amine | NH | CH3 | 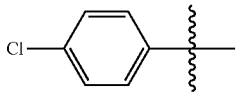 [SMILES: *c1ccc(Cl)cc1] | 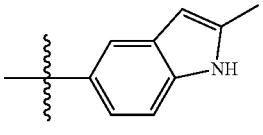 [SMILES: *c1ccc2[nH]c(C)cc2c1] |
| 114 | {1-[3-(4-Chloro-phenyl)-adamantan-1-yl]-ethyl}-(9-ethyl-9H-carbazol-3-yl)-amine | NH | CH3 | 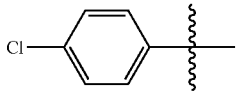 [SMILES: *c1ccc(Cl)cc1] | 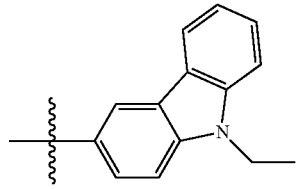 [SMILES: *c1ccc2c(c1)c1ccccc1n2CC] |
| 115 | {1-[3-(4-Chloro-phenyl)-adamantan-1-yl]-ethyl}-(9-ethyl-9H-carbazol-3-ylmethyl)-amine | NH | CH3 | 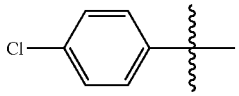 | 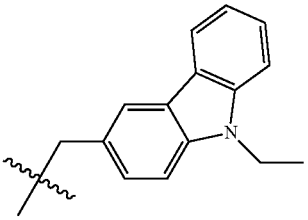 [SMILES: *Cc1ccc2c(c1)c1ccccc1n2CC] |
| 116 | 9-Ethyl-9H-carbazole-3-carboxylic acid {1-[3-(4-chloro-phenyl)-adamantan-1-yl]-ethyl}-amide | NH | CH3 | 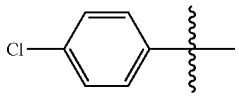 [SMILES: *c1ccc(Cl)cc1] | 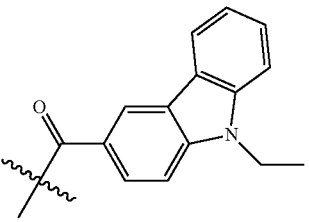 [SMILES: *C(=O)c1ccc2c(c1)c1ccccc1n2CC] |
| 117 | 1-{1-[3-(4-Chloro-phenyl)-adamantan-1-yl]-ethyl}-3-(4-chloro-3-trifluoromethyl-phenyl)-urea | NH | CH3 | 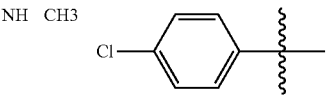 | 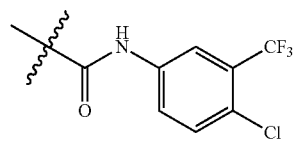 [SMILES: *C(=O)Nc1ccc(Cl)c(C(F)(F)F)c1] |
| 118 | 1-{1-[3-(4-Chloro-phenyl)-adamantan-1-yl]-ethyl}-3-(4-chloro-3-trifluoromethyl-phenyl)-urea | NH | CH3 | 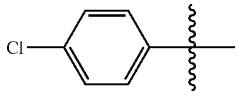 | 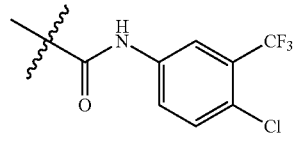 [SMILES: *C(=O)Nc1ccc(Cl)c(C(F)(F)F)c1] |

-continued

| Cmpd | Chemical name | Y | R3 | R1 | R2 |
|---|---|---|---|---|---|
| 119 | (4-Bromo-thiophen-2-ylmethyl)-{1-[3-(4-chloro-phenyl)-adamantan-1-yl]-ethyl}-amine | NH | CH3 | 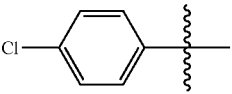 | 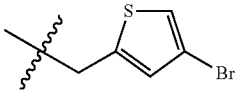 |
| 120 | {1-[3-(4-Chloro-phenyl)-adamantan-1-yl]-ethyl}-(4-phenyl-thiophen-2-ylmethyl)-amine | NH | CH3 | 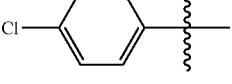 | 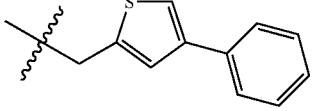 |

Representative formula I-1 compounds include:

| Cmpd | Chemical name | R1 | R2 |
|---|---|---|---|
| 121 | 3-Phenyl-adamantane-1-carboxylicacid | 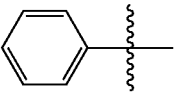 [SMILES: *c1ccccc1] | OH |
| 122 | 3-(4-Fluoro-phenyl)-adamantane-1-carboxylic acid | 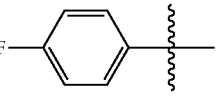 | OH |
| 123 | 3-(4-Chloro-phenyl)-adamantane-1-carboxylic acid | 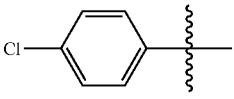 [SMILES: *c1ccc(Cl)cc1] | OH |
| 124 | 1-Adamantan-1-yl-ethanone | H | CH3 |
| 125 | 1-(3-Phenyl-adamantan-1-yl)-ethanone | 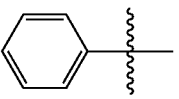 | CH3 |
| 126 | 1-[3-(4-Fluoro-phenyl)-adamantan-1-yl]-ethanone | 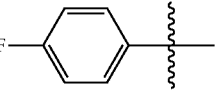 | CH3 |
| 127 | 1-[3-(4-Chloro-phenyl)-adamantan-1-yl]-ethanone | 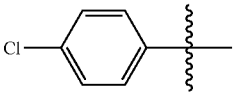 | CH3 |
| 128 | 2-(Adamantane-1-carbonyl)-malonicacid dimethyl ester | H | 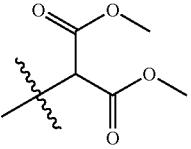 |
| 129 | 2-[3-(4-Chloro-phenyl)-adamantane-1-carbonyl]-malonic acid dimethylester | 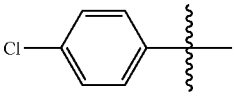 | 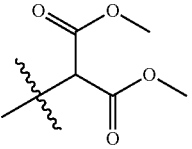 [SMILES: *C(C(=O)OC)C(=O)OC] |
| 130 | 3-(4-Chloro-phenyl)-1-[3-(4-chloro-phenyl)-adamantan-1-yl]-propenone | 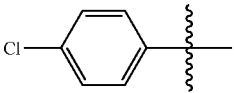 | 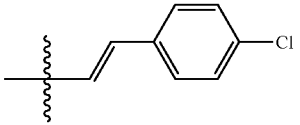 [SMILES: */C=C/c1ccc(Cl)nc1] |

| Cmpd | Chemical name | R1 | R2 |
|---|---|---|---|
| 131 | 4-{3-[3-(4-Chloro-phenyl)-adamantan-1-yl]-3-oxo-propenyl}-benzonitrile | Cl-C6H4- | -CH=CH-C6H4-CN |
| 132 | 1-[3-(4-Chloro-phenyl)-adamantan-1-yl]-3-(4-hydroxy-phenyl)-propenone | Cl-C6H4- | -CH=CH-C6H4-OH |
| 133 | 1-[3-(4-Chloro-phenyl)-adamantan-1-yl]-3-naphthalen-2-yl-propenone | Cl-C6H4- | -CH=CH-naphthalen-2-yl |
| 134 | 1-[3-(4-Chloro-phenyl)-adamantan-1-yl]-3-(6-chloro-pyridin-3-yl)-propenone | Cl-C6H4- | -CH=CH-(6-chloro-pyridin-3-yl) |
| 135 | 1-[3-(4-Chloro-phenyl)-adamantan-1-yl]-3-(1H-imidazol-4-yl)-propenone | Cl-C6H4- | -CH=CH-(1H-imidazol-4-yl) |
| 136 | 1-[3-(4-Chloro-phenyl)-adamantan-1-yl]-3-(9-ethyl-9H-carbazol-3-yl)-propenone | Cl-C6H4- | -CH=CH-(9-ethyl-9H-carbazol-3-yl) |
| 137 | 1-[3-(4-Chloro-phenyl)-adamantan-1-yl]-3-(4-phenyl-thiophen-2-yl)-propenone | Cl-C6H4- | -CH=CH-(4-phenyl-thiophen-2-yl) |

A particularly preferred aryladamantane compound of the present invention is illustrated below and referred to as ABC294640 [3-(4-chlorophenyl)-adamantane-1-carboxylic acid (pyridin-4-ylmethyl)amide]:

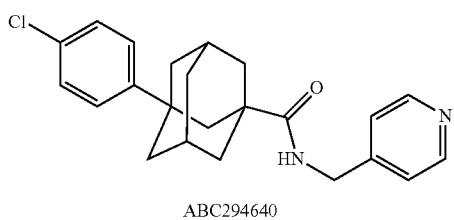 [SMILES: O=C(NCc1ccncc1)C12CC3CC(C1)CC(c1ccc(Cl)cc1)(C3)C2]

ABC294640

In an embodiment, an aryladamantane compound of the present invention is selected from a compound of Formula 8:

Formula 8

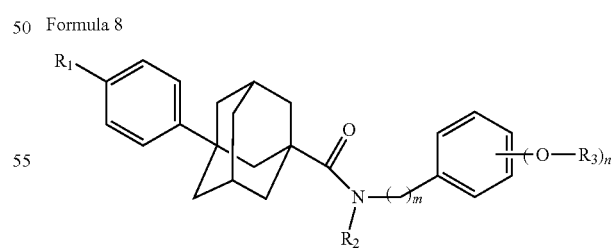

and pharmaceutically acceptable salts thereof, wherein
$R_1$ is H, Cl or F;
$R_2$ is H or alkyl;
m is 0, 1 or 2;
n is 1, 2, 3, 4 or 5;
each $R_3$ is independently H, —C(O)alkyl, —C(O)CH$_2$CH$_2$C(O)OH, $R_4$, —C(O)NR$_5$R$_6$, —P(O)(OR$_7$)$_2$ or glucosyl, provided that at least one $R_3$ is not H, wherein
R$_4$ is a natural or unnatural amino acid linked through the carboxyl moiety as an ester,
R$_5$ is H or alkyl,
R$_6$ is H or alkyl, and
each R$_7$ is independently H or alkyl.
In certain embodiments of the compounds of formula (I) as described above, the

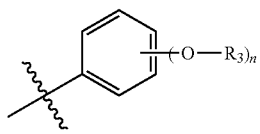

moiety is a catechol with substitution at least one catechol —OH. For example, in one embodiment, the

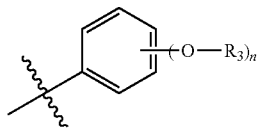

moiety has the structure

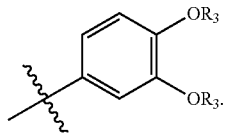

In one particularly preferred embodiment of the compounds of formula (I) as described above, the

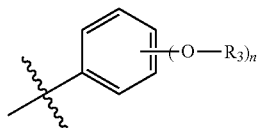

moiety has the structure

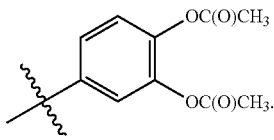

In one especially preferred embodiment of the invention, compounds of formula (I) have R$_1$=Cl, R$_2$=H, m=2, n=2, and each R$_3$=—C(O)alkyl, especially —C(O)CH$_3$.

For example, compounds of the invention include:
Acetic acid 2-acetoxy-5-(2-{[3-(4-chlorophenyl)-adamantane-1-carbonyl]-amino}ethyl)phenyl ester;
Propionic acid 2-propionyloxy-5-(2-{[3-(4-chlorophenyl)-adamantane-1-carbonyl]-amino}ethyl)phenyl ester;
Butyric acid 2-butyryloxy-5-(2-{[3-(4-chlorophenyl)-adamantane-1-carbonyl]-amino}ethyl)phenyl ester;
Isobutyric acid 5-(2-([3-(4-chlorophenyl)adamantane-1-carbonyl]amino)ethyl)-2-hydroxyphenyl ester; and
2-Amino-3-methyl-butyric acid 5-(2-{[3-(4-chlorophenyl)adamantane-1-carbonyl]amino}ethyl)-2-hydroxyphenyl ester.

A particularly preferred aryladamantane compound of the present invention is illustrated below and referred to as ABC294735 [3-(4-chlorophenyl)adamantane-1-carboxylic acid [2-(3,4-dihydroxyphenyl)ethyl]amide]:

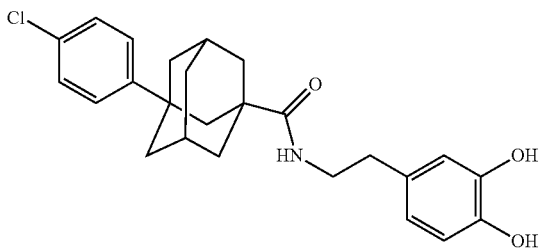

ABC294735

Solid forms for oral administration may contain pharmaceutically acceptable binders, sweeteners, disintegrating agents, diluents, flavorings, coating agents, preservatives, lubricants, and/or time delay agents. Suitable binders include gum acacia, gelatin, corn starch, gum tragacanth, sodium alginate, carboxymethylcellulose or polyethylene glycol (PEG). Suitable sweeteners include sucrose, lactose, glucose, aspartame or saccharine. Suitable disintegrating agents include corn starch, methylcellulose, polyvinylpyrrolidone, xanthan gum, bentonite, alginic acid or agar. Suitable diluents include lactose, sorbitol, mannitol, dextrose, kaolin, cellulose, calcium carbonate, calcium silicate or dicalcium phosphate. Suitable flavoring agents include peppermint oil, oil of wintergreen, cherry, orange, or raspberry flavoring. Suitable coating agents include polymers or copolymers of acrylic acid and/or methacrylic acid and/or their esters, waxes, fatty alcohols, zein, shellac or gluten. Suitable preservatives include sodium benzoate, vitamin E, alpha-tocopherol, ascorbic acid, methyl paraben, propyl paraben or sodium bisulphite. Suitable lubricants include magnesium stearate, stearic acid, sodium oleate, sodium chloride or talc. Suitable time delay agents include glyceryl monostearate or glyceryl distearate.

In an embodiment, the present disclosure relates to methods for treating a subject having a ssRNA viral infection, such as Ebola virus or Marburg virus, by concomitantly administering i) a therapeutically effective amount of an anti-viral drug; and ii) a therapeutically effective amount of at least one anti-atypical mycobacterial agent. In an embodiment, the anti-viral drug is Brivudine (BVDU), an active metabolite of BVDU, a salt thereof, or BVDU in protected or in prodrug form. Suitable anti-atypical mycobacterial agents include, but are not limited to, clarithromycin, rifabutin, rifampicin, azithromycin, roxithromycin, amikacin, clofazimine, ethambutol ofloxacin, ciprofloxacin and oxazolidinone. In an embodiment, the anti-atypical mycobacterial agents are selected from at least one of rifabutin, clarithromycin and clofazimine. In an embodiment, the anti-atypical mycobacterial agent is clofazimine. In an embodiment, the anti-atypical mycobacterial agent clofazimine is administered as a single solid oral dosage form.

In an embodiment, the present disclosure relates to methods for treating a subject having a ssRNA viral infection, such as Ebola virus, by concomitantly administering i) a therapeutically effective amount of an anti-viral drug; ii) a therapeutically effective amount of rifabutin; iii) a therapeutically effective amount of clofazimine; and iv) a therapeutically effective amount of clarithromycin. In an embodiment, the anti-viral drug is Brivudine (BVDU), an active metabolite of BVDU, a salt thereof, or BVDU in protected or in prodrug form.

In an embodiment, the present disclosure relates to methods for treating a subject having a ssRNA viral infection, e.g., but not limited to, Ebola virus, by concomitantly administering i) a therapeutically effective amount of an anti-viral and ii) a therapeutically effective amount of clofazamine. In an embodiment, the anti-viral drug is Brivudine (BVDU), an active metabolite of BVDU, a salt thereof, or BVDU in protected or in prodrug form.

In an embodiment, the present disclosure relates to methods for treating a subject having a ssRNA viral infection, e.g., but not limited to, Ebola virus, by concomitantly administering i) a therapeutically effective amount of an anti-viral drug; ii) a therapeutically effective amount of rifabutin; and iii) a therapeutically effective amount of clofazimine. In an embodiment, the anti-viral drug is Brivudine (BVDU), an active metabolite of BVDU, a salt thereof, or BVDU in protected or in prodrug form. In an embodiment, the rifabutin and the clofazimine are administered as a single solid oral dosage form. In an embodiment, rifabutin and clofazimine are administered as separate solid oral dosage forms.

In an embodiment, the present disclosure relates to methods for treating a subject having a ssRNA viral infection, e.g., but not limited to, Ebola virus, by concomitantly administering i) a therapeutically effective amount of brivudine, an active metabolite of brivudine (BVDU), an active metabolite of BVDU, a salt thereof, or BVDU in protected or in prodrug form and ii) a therapeutically effective amount of clarithromycin as an intravenous infusion.

In an embodiment, the present disclosure relates to methods for treating a subject having a ssRNA viral infection, e.g., but not limited to, Ebola virus, by administering a therapeutically effective amount of an aryladamantane compound. In an embodiment the aryladamantane compound is selected from a compound of formula 7.

In an embodiment, the present disclosure relates to methods for treating a subject having a ssRNA viral infection, e.g., but not limited to, Ebola virus, by concomitantly administering i) a therapeutically effective amount of brivudine, an active metabolite of brivudine (BVDU), an active metabolite of BVDU, a salt thereof, or BVDU in protected or in prodrug form and ii) a therapeutically effective amount of an aryladamantane compound. In an embodiment the aryladamantane compound is selected from a compound of formula 7.

In an embodiment, the present disclosure relates to methods for treating a subject having a ssRNA viral infection, such as Ebola virus or Marburg virus, by concomitantly administering i) a therapeutically effective amount of an anti-viral drug; ii) a therapeutically effective amount of at least one anti-atypical mycobacterial agent; and iii) a therapeutically effective amount of an aryladamantane compound. In an embodiment, the anti-viral drug is Brivudine (BVDU), an active metabolite of BVDU, a salt thereof, or BVDU in protected or in prodrug form. Suitable anti-atypical mycobacterial agents include, but are not limited to, clarithromycin, rifabutin, rifampicin, azithromycin, roxithromycin, amikacin, clofazimine, ethambutol ofloxacin, ciprofloxacin and oxazolidinone. In an embodiment, the anti-atypical mycobacterial agents are selected from at least one of rifabutin, clarithromycin and clofazimine. In an embodiment, the anti-atypical mycobacterial agent is clofazimine. In an embodiment, the anti-atypical mycobacterial agent clofazimine is administered as a single solid oral dosage form. In an embodiment the aryladamantane compound is selected from a compound of formula 7.

In an embodiment, a treatment for a ssRNA viral infection, such as Ebola virus includes providing intravenous fluids (IV) and balancing electrolytes (body salts) to a subject; maintaining oxygen status and blood pressure of the subject; and concomitantly administering i) a therapeutically effective amount of an anti-viral drug; ii) a therapeutically effective amount of rifabutin; iii) a therapeutically effective amount of clofazimine; and iv) a therapeutically effective amount of clarithromycin. In an embodiment, the anti-viral drug is Brivudine (BVDU), an active metabolite of BVDU, a salt thereof, or BVDU in protected or in prodrug form.

In an embodiment, a treatment for a ssRNA viral infection, e.g., but not limited to, Ebola virus, includes providing intravenous fluids (IV) and balancing electrolytes (body salts) to a subject; maintaining oxygen status and blood pressure of the subject; and concomitantly administering i) a therapeutically effective amount of an anti-viral drug; and ii) a therapeutically effective amount of clofazimine. In an embodiment, the anti-viral drug is Brivudine (BVDU), an active metabolite of BVDU, a salt thereof, or BVDU in protected or in prodrug form.

In an embodiment, a treatment for a ssRNA viral infection, e.g., but not limited to, Ebola virus, includes providing intravenous fluids (IV) and balancing electrolytes (body salts) to a subject; maintaining oxygen status and blood pressure of the subject; and concomitantly administering i) a therapeutically effective amount of an anti-viral drug; ii) a therapeutically effective amount of clofazimine; and iii) a therapeutically effective amount of rifabutin. In an embodiment, the anti-viral drug is Brivudine (BVDU), an active metabolite of BVDU, a salt thereof, or BVDU in protected or in prodrug form. In an embodiment, the rifabutin and the clofazimine are administered as a single solid oral dosage form. In an embodiment, rifabutin and clofazimine are administered as separate solid oral dosage forms.

In an embodiment, a treatment for a ssRNA viral infection, e.g., but not limited to, Ebola virus, includes providing intravenous fluids (IV) and balancing electrolytes (body salts) to a subject; maintaining oxygen status and blood pressure of the subject; and concomitantly administering i) a therapeutically effective amount of an anti-viral drug; and ii) a therapeutically effective amount of clarithromycin as an intravenous infusion. In an embodiment, the anti-viral drug is Brivudine (BVDU), an active metabolite of BVDU, a salt thereof, or BVDU in protected or in prodrug form.

In an embodiment, a treatment for a ssRNA viral infection, e.g., but not limited to, Ebola virus, includes providing intravenous fluids (IV) and balancing electrolytes (body salts) to a subject; maintaining oxygen status and blood pressure of the subject; and administering a therapeutically effective amount of an aryladamantane compound. In an embodiment the aryladamantane compound is selected from a compound of formula 7.

In an embodiment, a treatment for a ssRNA viral infection, e.g., but not limited to, Ebola virus, includes providing intravenous fluids (IV) and balancing electrolytes (body salts) to a subject; maintaining oxygen status and blood pressure of the subject; and concomitantly administering i) a therapeutically effective amount of an anti-viral drug; and ii) a therapeutically effective amount of at least one anti-atypical mycobacterial agent. In an embodiment, the antiviral drug is Brivudine (BVDU), an active metabolite of BVDU, a salt thereof, or BVDU in protected or in prodrug form. Suitable anti-atypical mycobacterial agents include, but are not limited to, clarithromycin, rifabutin, rifampicin, azithromycin, roxithromycin, amikacin, clofazimine, ethambutol ofloxacin, ciprofloxacin and oxazolidinone. In an embodiment, the anti-atypical mycobacterial agents are selected from at least one of rifabutin, clarithromycin and clofazimine. In an embodiment, the anti-atypical mycobacterial agent is clofazimine. In an embodiment, the anti-atypical mycobacterial agent clofazimine is administered as a single solid oral dosage form.

In an embodiment, a treatment for a ssRNA viral infection, e.g., but not limited to, Ebola virus, includes providing intravenous fluids (IV) and balancing electrolytes (body salts) to a subject; maintaining oxygen status and blood pressure of the subject; and concomitantly administering i) a therapeutically effective amount of an anti-viral drug; ii) a therapeutically effective amount of at least one anti-atypical mycobacterial agent; and iii) a therapeutically effective amount of an aryladamantane compound. In an embodiment, the anti-viral drug is Brivudine (BVDU), an active metabolite of BVDU, a salt thereof, or BVDU in protected or in prodrug form. Suitable anti-atypical mycobacterial agents include, but are not limited to, clarithromycin, rifabutin, rifampicin, azithromycin, roxithromycin, amikacin, clofazimine, ethambutol ofloxacin, ciprofloxacin and oxazolidinone. In an embodiment, the anti-atypical mycobacterial agents are selected from at least one of rifabutin, clarithromycin and clofazimine. In an embodiment, the anti-atypical mycobacterial agent is clofazimine. In an embodiment, the anti-atypical mycobacterial agent clofazimine is administered as a single solid oral dosage form. In an embodiment the aryladamantane compound is selected from a compound of formula 7.

If desired, the compounds of the invention may be employed in mechanistic assays to determine whether other combinations, or single agents, are as effective as the combinations of the invention in inhibiting a viral disease (e.g., those described herein) using assays generally known in the art. For example, candidate compounds may be tested, alone or in combination (e.g., with an agent that inhibits viral replication, such as those described herein) and applied to cells (e.g., hepatic cells such as HepG2, kidney epithelial cells such as 293T, macrophages such as THP-1, or isolated primary cells). After a suitable time, viral replication or load of these cells is examined. A decrease in viral replication or viral load identifies a candidate compound or combination of agents as an effective agent for treating a viral disease.

The compositions and methods of the invention can include formulation(s) of compound(s) that, upon administration to a subject, result in a concentration of the compound(s) that treats a filovirus-mediated disease. The compound(s) may be contained in any appropriate amount in any suitable carrier substance, and are generally present in an amount of 1-95% by weight of the total weight of the composition. The composition may be provided in a dosage form that is suitable for the oral, parenteral (e.g., intravenously or intramuscularly), rectal, dermatological, cutaneous, nasal, vaginal, inhalant, skin (patch), ocular, intrathecal, or intracranial administration route. Thus, the composition may be in the form of, e.g., tablets, capsules, pills, powders, granulates, suspensions, emulsions, solutions, gels including hydrogels, pastes, ointments, creams, plasters, drenches, osmotic delivery devices, suppositories, enemas, injectables, implants, sprays, or aerosols. The pharmaceutical compositions may be formulated according to conventional pharmaceutical practice.

Pharmaceutical compositions according to the invention or used in the methods of the invention may be formulated to release the active compound immediately upon administration or at any predetermined time or time period after administration. The latter types of compositions are generally known as controlled release formulations, which include (i) formulations that create substantially constant concentrations of the agent(s) of the invention within the body over an extended period of time; (ii) formulations that after a predetermined lag time create substantially constant concentrations of the agent(s) of the invention within the body over an extended period of time; (iii) formulations that sustain the agent(s) action during a predetermined time period by maintaining a relatively constant, effective level of the agent(s) in the body with concomitant minimization of undesirable side effects associated with fluctuations in the plasma level of the agent(s) (sawtooth kinetic pattern); (iv) formulations that localize action of agent(s), e.g., spatial placement of a controlled release composition adjacent to or in the diseased tissue or organ; (v) formulations that achieve convenience of dosing, e.g., administering the composition once per week or once every two weeks; and (vi) formulations that target the action of the agent(s) by using carriers or chemical derivatives to deliver the combination to a particular target cell type.

Any of a number of strategies can be pursued in order to obtain controlled release in which the rate of release outweighs the rate of metabolism of the compound in question. In one example, controlled release is obtained by appropriate selection of various formulation parameters and ingredients, including, e.g., various types of controlled release compositions and coatings. Thus, the compound(s) are formulated with appropriate excipients into a pharmaceutical composition that, upon administration, releases the compound(s) in a controlled manner. Examples include single or multiple unit tablet or capsule compositions, oil solutions, suspensions, emulsions, microcapsules, molecular complexes, microspheres, nanoparticles, patches, and liposomes.

It is not intended that administration of compounds be limited to a single formulation and delivery method for all compounds of a combination. The combination can be administered using separate formulations and/or delivery methods for each compound of the combination using, for example, any of the above-described formulations and methods. In one example, a first agent is delivered orally, and a second agent is delivered intravenously.

The dosage of a compound or a combination of compounds depends on several factors, including: the administration method, the type of disease to be treated, the severity of the infection, whether administration first occurs at an early or late stage of infection, and the age, weight, and health of the patient to be treated. For combinations that include a synergistic pair of agents identified herein, the recommended dosage for the anti-viral agent can be less than or equal to the recommended dose as given in the Physician's Desk Reference, $69^{th}$ Edition (2015).

As described above, the compound(s) in question may be administered orally in the form of tablets, capsules, elixirs or syrups, or rectally in the form of suppositories. Parenteral administration of a compound is suitably performed, for example, in the form of saline solutions or with the compound(s) incorporated into liposomes. In cases where the compound in itself is not sufficiently soluble to be dissolved, a solubilizer such as ethanol can be applied. The correct dosage of a compound can be determined by examining the efficacy of the compound in viral replication assays, as well as its toxicity in humans.

The agents of the invention are also useful tools in elucidating mechanistic information about the biological pathways involved in viral diseases. Such information can lead to the development of new combinations or single agents for treating, preventing, or reducing a viral disease. Methods known in the art to determine biological pathways can be used to determine the pathway, or network of pathways affected by contacting cells (e.g., primary macrophage cells) infected with a virus with the compounds of the invention. Such methods can include, analyzing cellular constituents that are expressed or repressed after contact with the compounds of the invention as compared to untreated, positive or negative control compounds, and/or new single agents and combinations, or analyzing some other activity of the cell or virus such as an enzymatic activity, nutrient uptake, and proliferation. Cellular components analyzed can include gene transcripts, and protein expression. Suitable methods can include standard biochemistry techniques, radiolabeling the compounds of the invention (e.g., $^{14}C$ or $^{3}H$ labeling), and observing the compounds binding to proteins, e.g., using 2D gels, gene expression profiling. Once identified, such compounds can be used in in vivo models (e.g., knockout or transgenic mice) to further validate the tool or develop new agents or strategies to treat viral disease.

EXAMPLES

The following examples are intended to illustrate rather than limit the invention.

Example 1: In Vitro Screening Experiments

A screening experiment, the in-vitro plaque assay, provided results regarding measurable inhibition of replication of ssRNA viruses in cell culture.

In order to perform the assay, primary human macrophage cells were seeded at $1 \times 10^5$ cells/well in 100 µl 10% RPMI 1640 medium (Biocoat collagen I-coated 96 well plates). The next day, the medium was removed and 100 µl of medium containing different concentrations of drugs was added for one (1) hour. Afterwards, 15 µl of virus medium mixture was added to each well for one (1) hour (multiplicity of infection (MOI) of either 0.01, 0.1 or 1.0). The virus inoculars were removed and 100 µl of medium containing different concentrations of drugs was added. The plates were kept at 37° C. incubator for 48 h. After 48 h post infection, the supernatants were harvested for plaque assay and the plates were fixed with 10% NBF. 7. The plates were then stained with anti-EBOV VP40. The plates were washed three (3) times with PBS to remove NBF. Cells were permeablized with 0.25% Triton X-100 in PBS for 5 minutes at room temperature. The plates were again washed three (3) times with PBS, and then blocked with 10% BSA in PBS for 30 minutes at 37° C. The cells were stained with primary antibody (anti-EBOV Vp40 BMD004B007) at 1:1000 in 3% BSA (in PBS) for 2 h at 37° C. The plates were again washed three (3) times with PBS and stained with a secondary antibody (Alex-488 conjugated goat anti-mouse IgG) at 1:2000 in 3% BSA (in PBS) for 45 minutes at 37° C. The plates were again washed three (3) times with PBS and cells were stained with Horst for 10 minutes at room temperature. Plates were washed three (3) times with PBS and then scanned using the PerkinElmer Operetta® High Content Imaging System. The percentage of infected cells was measured and analyzed using the Operetta® High Content Imaging System with Harmony® High Content Imaging and Analysis Software.

Primary human macrophage cells were seeded at $1 \times 10^5$ cells/well in 100 µl 10% RPMI 1640 medium (Biocoat collagen I-coated 96 well plates). The next day, the medium was removed and 100 µl medium containing different concentration of drugs was added. 48 h post treatment, cytotoxicity was measured using Dojindo's Cell Counting Kit-8 (CCK-8), which utilizes Dojindo's highly water-soluble tetrazolium salt (WST). WST-8 produces a water-soluble formazan dye upon reduction in the presence of an electron mediator. The viability was calculated with regard to the untreated cell control, which was set to 100% viability.

The assays described above were used to identify drugs that inhibit the replication of Ebola virus in primary human macrophage cells.

The Table below provides a listing of the concentration of drugs and drug combinations tested and their effect on primary human macrophage cell toxicity.

| Drug(s) | concentration | Cytotoxic to Primary Human Macrophage Cells? |
|---|---|---|
| Clofazamine | 6 µM | No |
| Clofazamine | 7 µM | No |
| Clofazamine | 8 µM | No |
| Clofazamine | 9 µM | No |
| Rifabutin | 30 µM | No |
| Rifabutin | 45 µM | No |
| Rifabutin | 60 µM | No |
| Rifabutin | 75 µM | Yes |
| Rifabutin | 90 µM | Yes |
| Rifabutin | 120 µM | Yes |
| Rifabutin | 150 µM | Yes |
| Rifabutin | 180 µM | Yes |
| Rifabutin | 210 µM | Yes |
| Rifabutin | 240 µM | Yes |
| Rifabutin | 270 µM | Yes |
| Rifabutin | 300 µM | Yes |
| Rifabutin | 330 µM | Yes |
| Rifabutin | 360 µM | Yes |
| Clarithromycin | 60 µM | No |
| Clarithromycin | 75 µM | No |
| Clarithromycin | 90 µM | No |
| Clarithromycin | 120 µM | No |
| Clarithromycin | 150 µM | No |
| Clarithromycin | 180 µM | No |
| Clarithromycin | 210 µM | No |
| Clarithromycin | 240 µM | Yes |
| Clarithromycin | 270 µM | Yes |
| Clarithromycin | 300 µM | Yes |
| Clarithromycin | 330 µM | Yes |
| Clarithromycin | 360 µM | Yes |
| Brivudine | 90 µM | No |
| Brivudine | 120 µM | No |
| Brivudine | 150 µM | No |
| Brivudine | 180 µM | No |
| Brivudine | 210 µM | No |
| Brivudine | 240 µM | No |
| Brivudine | 270 µM | No |
| Brivudine | 300 µM | Yes |
| Brivudine | 330 µM | Yes |
| Brivudine | 360 µM | Yes |
| ABC29460 | 2.5 µM | No |
| ABC29460 | 5.0 µM | No |
| ABC29460 | 10 µM | No |
| ABC29460 | 20 µM | Yes |
| ABC29460 | 40 µM | Yes |
| ABC29460 | 60 µM | Yes |
| ABC29460 | 80 µM | Yes |
| ABC29460 | 100 µM | Yes |
| Clarithromycin | 210 µM | No |
| Brivudine | 270 µM | |

-continued

| Drug(s) concentration | | Cytotoxic to Primary Human Macrophage Cells? |
|---|---|---|
| Rifabutin | 45 μM | No |
| Clarithromycin | 75 μM | |
| Rifabutin | 45 μM | No |
| Clarithromycin | 90 μM | |
| Rifabutin | 45 μM | No |
| Clarithromycin | 120 μM | |
| Rifabutin | 45 μM | No |
| Clarithromycin | 150 μM | |
| Rifabutin | 45 μM | No |
| Clarithromycin | 180 μM | |
| Rifabutin | 45 μM | No |
| Clarithromycin | 210 μM | |
| Rifabutin | 60 μM | Yes |
| Clarithromycin | 210 μM | |
| Rifabutin | 60 μM | Yes |
| Brivudine | 270 μM | |
| Rifabutin | 60 μM | Yes |
| Clarithromycin | 210 μM | |
| Brivudine | 270 μM | |
| Clofazamine | 13.2 μM | Yes |
| Rifabutin | 31.8 μM | |
| Clarithromycin | 76.2 μM | |
| Clofazamine | 11 μM | Yes |
| Rifabutin | 26.5 μM | |
| Clarithromycin | 63.5 μM | |
| Clofazamine | 8.8 μM | Yes |
| Rifabutin | 21.2 μM | |
| Clarithromycin | 50.8 μM | |
| Clofazamine | 6.6 μM | No |
| Rifabutin | 15.9 μM | |
| Clarithromycin | 38.1 μM | |
| Clofazamine | 4.4 μM | No |
| Rifabutin | 10.6 μM | |
| Clarithromycin | 25.4 μM | |
| Clofazamine | 2.2 μM | No |
| Rifabutin | 5.3 μM | |
| Clarithromycin | 12.7 μM | |
| Clofazamine | 1.1 μM | No |
| Rifabutin | 2.65 μM | |
| Clarithromycin | 6.35 μM | |
| Clofazamine | 0.66 μM | No |
| Rifabutin | 1.59 μM | |
| Clarithromycin | 3.81 μM | |
| Clofazamine | 0.22 μM | No |
| Rifabutin | 0.53 μM | |
| Clarithromycin | 1.27 μM | |
| Clofazamine | 0.11 μM | No |
| Rifabutin | 0.265 μM | |
| Clarithromycin | 0.635 μM | |
| Clofazamine | 13.2 μM | Yes |
| Rifabutin | 31.8 μM | |
| Brivudine | 90.0 μM | |
| Clofazamine | 11 μM | Yes |
| Rifabutin | 26.5 μM | |
| Brivudine | 75.0 μM | |
| Clofazamine | 8.8 μM | Yes |
| Rifabutin | 21.2 μM | |
| Brivudine | 60.0 μM | |
| Clofazamine | 6.6 μM | No |
| Rifabutin | 15.91 μM | |
| Brivudine | 45.0 μM | |
| Clofazamine | 4.4 μM | No |
| Rifabutin | 10.6 μM | |
| Brivudine | 30.0 μM | |
| Clofazamine | 2.2 μM | No |
| Rifabutin | 5.3 μM | |
| Brivudine | 15.0 μM | |
| Clofazamine | 1.1 μM | No |
| Rifabutin | 2.65 μM | |
| Brivudine | 7.5 μM | |
| Clofazamine | 0.66 μM | No |
| Rifabutin | 1.59 μM | |
| Brivudine | 4.5 μM | |
| Clofazamine | 0.22 μM | No |
| Rifabutin | 0.53 μM | |
| Brivudine | 1.5 μM | |

-continued

| Drug(s) concentration | | Cytotoxic to Primary Human Macrophage Cells? |
|---|---|---|
| Clofazamine | 0.11 μM | No |
| Rifabutin | 0.265 μM | |
| Brivudine | 0.75 μM | |
| Rifabutin | 31.8 μM | No |
| Clarithromycin | 76.2 μM | |
| Brivudine | 90 μM | |
| Rifabutin | 26.5 μM | No |
| Clarithromycin | 63.5 μM | |
| Brivudine | 75 μM | |
| Rifabutin | 21.2 μM | No |
| Clarithromycin | 50.8 μM | |
| Brivudine | 60 μM | |
| Rifabutin | 15.9 μM | No |
| Clarithromycin | 38.1 μM | |
| Brivudine | 45 μM | |
| Rifabutin | 10.6 μM | No |
| Clarithromycin | 25.4 μM | |
| Brivudine | 30 μM | |
| Rifabutin | 5.3 μM | No |
| Clarithromycin | 12.7 μM | |
| Brivudine | 15 μM | |
| Rifabutin | 2.65 μM | No |
| Clarithromycin | 6.35 μM | |
| Brivudine | 7.5 μM | |
| Rifabutin | 1.59 μM | No |
| Clarithromycin | 3.81 μM | |
| Brivudine | 4.5 μM | |
| Rifabutin | 0.53 μM | No |
| Clarithromycin | 1.27 μM | |
| Brivudine | 1.5 μM | |
| Rifabutin | 0.265 μM | No |
| Clarithromycin | 0.635 μM | |
| Brivudine | 0.75 μM | |
| Clofazamine | 13.2 μM | Yes |
| Clarithromycin | 76.2 μM | |
| Brivudine | 90 μM | |
| Clofazamine | 11 μM | Yes |
| Clarithromycin | 63.5 μM | |
| Brivudine | 75 μM | |
| Clofazamine | 8.8 μM | Yes |
| Clarithromycin | 50.8 μM | |
| Brivudine | 60 μM | |
| Clofazamine | 6.6 μM | No |
| Clarithromycin | 38.1 μM | |
| Brivudine | 45 μM | |
| Clofazamine | 4.4 μM | No |
| Clarithromycin | 25.4 μM | |
| Brivudine | 30 μM | |
| Clofazamine | 2.2 μM | No |
| Clarithromycin | 12.7 μM | |
| Brivudine | 15 μM | |
| Clofazamine | 1.1 μM | No |
| Clarithromycin | 6.35 μM | |
| Brivudine | 7.5 μM | |
| Clofazamine | 0.66 μM | No |
| Clarithromycin | 3.81 μM | |
| Brivudine | 4.5 μM | |
| Clofazamine | 0.22 μM | No |
| Clarithromycin | 1.27 μM | |
| Brivudine | 1.5 μM | |
| Clofazamine | 0.11 μM | No |
| Clarithromycin | 0.635 μM | |
| Brivudine | 0.75 μM | |
| Rifabutin | 45 μM | Yes |
| Clarithromycin | 210 μM | |
| Rifabutin | 45 μM | No |
| Clarithromycin | 180 μM | |
| Rifabutin | 45 μM | No |
| Clarithromycin | 150 μM | |
| Rifabutin | 45 μM | No |
| Clarithromycin | 120 μM | |
| Rifabutin | 45 μM | No |
| Clarithromycin | 90 μM | |
| Rifabutin | 45 μM | No |
| Clarithromycin | 75 μM | |

-continued

| Drug(s) concentration | | Cytotoxic to Primary Human Macrophage Cells? |
|---|---|---|
| Rifabutin | 60 μM | Yes |
| Clarithromycin | 210 μM | |
| Rifabutin | 60 μM | Yes |
| Clarithromycin | 180 μM | |
| Rifabutin | 60 μM | Yes |
| Clarithromycin | 150 μM | |
| Rifabutin | 60 μM | Yes |
| Clarithromycin | 120 μM | |
| Rifabutin | 60 μM | No |
| Clarithromycin | 90 μM | |
| Rifabutin | 60 μM | No |
| Clarithromycin | 75 μM | |
| Rifabutin | 31.8 μM | Yes |
| Clarithromycin | 76.2 μM | |
| ABC29460 | 100 μM | |
| Rifabutin | 31.8 μM | Yes |
| Clarithromycin | 76.2 μM | |
| ABC29460 | 80 μM | |
| Rifabutin | 31.8 μM | Yes |
| Clarithromycin | 76.2 μM | |
| ABC29460 | 60 μM | |
| Rifabutin | 31.8 μM | Yes |
| Clarithromycin | 76.2 μM | |
| ABC29460 | 40 μM | |
| Rifabutin | 31.8 μM | Yes |
| Clarithromycin | 76.2 μM | |
| ABC29460 | 20 μM | |
| Rifabutin | 31.8 μM | Yes |
| Clarithromycin | 76.2 μM | |
| ABC29460 | 10 μM | |
| Rifabutin | 31.8 μM | Yes |
| Clarithromycin | 76.2 μM | |
| ABC29460 | 5 μM | |
| Rifabutin | 31.8 μM | Yes |
| Clarithromycin | 76.2 μM | |
| ABC29460 | 2.5 μM | |

Based on these results, specific concentrations and combinations of drugs were tested to determine whether or not they were capable of inhibiting replication of Ebola virus.

The Table below provides a summary of the concentration of drugs and drug combinations that were found to be both non-toxic and provide a reduction in the infection of Ebola virus on primary macrophage cells.

| MOI = 0.01, 0.1 and 1.0 |
|---|
| Clofazamine 6 μm |
| Rifabutin 60 μm |
| Clarithromycin 210 μm + Brivudine 270 μm |
| Rifabutin 31.8 μm + Clarithromycin 76.2 μm |
| Rifabutin 31.8 μm + Clarithromycin 76.2 μm + Brivudine 90 μm |
| Rifabutin 31.8 μm + Clarithromycin 76.2 μm + Brivudine 150 μm |
| Rifabutin 31.8 μm + Clarithromycin 76.2 μm + Brivudine 210 μm |

| MOI = 0.1 |
|---|
| Rifabutin 45 μm + Clarithromycin 180 μm |
| Rifabutin 45 μm + Clarithromycin 150 μm |
| Rifabutin 45 μm + Clarithromycin 120 μm |
| Rifabutin 45 μm + Clarithromycin 90 μm |
| Rifabutin 45 μm + Clarithromycin 75 μm |
| Rifabutin 60 μm + Clarithromycin 90 μm |
| Rifabutin 60 μm + Clarithromycin 75 μm |
| Clarithromycin 75 μm |
| Clarithromycin 90 μm |
| Clarithromycin 120 μm |
| Clarithromycin 150 μm |
| Clarithromycin 180 μm |
| ABC294640 2.5 μm |
| ABC294640 5.0 μm |
| ABC294640 10.0 μm |

| MOI = 1 |
|---|
| Rifabutin 26.5 μm + Clarithromycin 63.5 μm + Brivudine 75 μm |

Clarithromycin alone can inhibit EBOV infection in primary macrophages. There appears to be a synergistic effect when rifabutin and clarithromycin are administered together.

Prophetic Examples

Example 2: In Vivo Screening Experiments—Ebola—Nonhuman Primates

Rhesus macaques will be used to determine whether administration of an agent of the present invention or a combination of agents of the present invention for a suitable period of time are capable of inhibiting viral replication, decreasing viral load, or reducing at least one symptom associated with Ebola. The experiment will consist of the same number of nonhuman primates (NHPs) per study arm receiving various doses of agents of the present invention alone and agents of the present invention together for a suitable period of time, beginning at least one day after a lethal intramuscular challenge with, for example, 4,000× median tissue culture infective dose ($TCID_{50}$) (or 2,512 plaque-forming units (p.f.u.) of EBOV-K. It is contemplated that the NHPs from each study arm will be split up into different groups that will receive the agent or agents at different time points post infection, such as 30 to 75 min (Group 1), 24 hours (Group 2), 48 hours (Group 3), and 72 hours (Group 4) after infection, and will comprise at least one daily dose. Control animals consisting of the same number of NHPs as the study arm will be given phosphate-buffered saline (PBS). Kaplan-Meier survival curves for each Group will be created and clinical scores and fever (rectal temperature) will be measured. In addition, viral titres (EBOC viraemia) by $TCID_{50}$ will be measured. Blood counts and serum biochemistry, including, but not limited to, white blood cell count, lymphocyte count, lymphocyte percentage, platelet count, neutrophil count, neutrophil percentage, alanine aminotransferase, alkaline phosphatase, blood urea nitrogen, creatinine and glucose, will be measured.

Example 3: In Vivo Screening Experiments—Marburg—Nonhuman Primates

Rhesus macaques will be used to determine whether administration of an agent of the present invention or a combination of agents of the present invention for a suitable period of time are capable of inhibiting viral replication, decreasing viral load, or reducing at least one symptom associated with Marburg. The experiment will consist of the same number of nonhuman primates (NHPs) per study arm receiving various doses of agents of the present invention alone and agents of the present invention together for a suitable period of time, beginning at least one day after a lethal dose of MARV-Angola. It is contemplated that the NHPs from each study arm will be split up into different groups that will receive the agent or agents at different time points post infection, such as 30 to 75 min (Group 1), 24 hours (Group 2), 48 hours (Group 3), and 72 hours (Group 4) after infection, and will comprise at least one daily dose.

Control animals consisting of the same number of NHPs as the study arm will be given phosphate-buffered saline (PBS). Kaplan-Meier survival curves for each Group will be created and clinical scores and fever (rectal temperature) will be measured. In addition, viral titres by $TCID_{50}$ will be measured. Blood counts and serum biochemistry, including, but not limited to, white blood cell count, lymphocyte count, lymphocyte percentage, platelet count, neutrophil count, neutrophil percentage, alanine aminotransferase, alkaline phosphatase, blood urea nitrogen, creatinine and glucose, will be measured.

A method of the present invention includes administering a compound to an individual infected with or exposed to a filovirus, wherein the step of administering is carried out for a suitable time period so that the individual is treated, and wherein the compound is represented by formula I:

(I)

or a pharmaceutically acceptable salt thereof, wherein:

$R_1$ is phenyl, 4-chlorophenyl or 4-fluorophenyl, $R_2$ is 4-pyridyl, optionally substituted with up to 4 groups that are independently ($C_1$-$C_6$) alkyl, halogen, haloalkyl, —OC(O)($C_1$-$C_6$ alkyl), —C(O)O($C_1$-$C_6$ alkyl), —CONR'R", —OC(O)NR'R", —NR'C(O)R", —$CF_3$, —$OCF_3$, —OH, $C_1$-$C_6$ alkoxy, hydroxyalkyl, —CN, —$CO_2$H, —SH, —S-alkyl, —SOR'R", —$SO_2$R', —$NO_2$, or NR'R", wherein R' and R" are independently H or ($C_1$-$C_6$) alkyl, and wherein each alkyl portion of a substituent is optionally further substituted with 1, 2, or 3 groups independently selected from halogen, CN, OH, and $NH_2$, $R_4$ is H or alkyl, and n is 1 or 2; and determining whether the individual has been treated, wherein the step of determining comprising one of measuring an inhibition in viral replication, measuring a decrease in viral load, or reducing at least one symptom associated with the filovirus. In an embodiment, the compound of formula I is:

3-(4-Chloro-phenyl)-adamantane-1-carboxylic acid (pyridin-4-ylmethyl)-amide

In an embodiment, an effective amount of the compound of formula I is between about 15.0 mg/kg/day to about 20 mg/kg/day. In an embodiment, the determining step includes measuring, at at least two different times during the suitable time period, the viral load using a nucleic acid amplification based test. In an embodiment, the inhibition in viral replication or the decrease in viral load is at least 10% as determined using a nucleic acid amplification based test. In an embodiment, the individual is a human. In an embodiment, the filovirus is Ebola virus or Marburg virus. In an embodiment, the filovirus is Ebola virus. In an embodiment, the compound of formula I is present as a solid dosage form. In an embodiment, the solid dosage form is a capsule. In an embodiment, the method further includes administering at least one antibiotic to the individual infected with or exposed to the filovirus for the suitable time period, wherein the combination of the at least one antibiotic and the compound of formula I produce a synergistic effect. In an embodiment, the at least one antibiotic is selected from one of clarithromycin or rifabutin.

A method of the present invention includes administering at least two antibiotics to an individual infected with or exposed to a filovirus, wherein the step of administering is carried out for a suitable time period so that the individual is treated; and determining whether the individual has been treated, wherein the step of determining includes one of measuring an inhibition in viral replication, measuring a decrease in viral load, or reducing at least one symptom associated with the filovirus. In an embodiment, at least one of the antibiotics is a macrolide antibiotic. In an embodiment, at least one of the antibiotics is a rifamycin antibiotic. In an embodiment, the antibiotics are clarithromycin and rifabutin. In an embodiment, an effective amount of clarithromycin is between about 12.0 mg/kg/day to about 17.0 mg/kg/day. In an embodiment, an effective amount of rifabutin is between about 4.0 mg/kg/day to about 8.0 mg/kg/day. In an embodiment, the determining step includes measuring, at at least two different times during the suitable time period, the viral load using a nucleic acid amplification based test. In an embodiment, the inhibition in viral replication or the decrease in viral load is at least 10% as determined using a suitable assay. In an embodiment, the individual is a human. In an embodiment, the filovirus is Ebola virus or Marburg virus. In an embodiment, the filovirus is Ebola virus.

All patents, patent applications, and published references cited herein are hereby incorporated by reference in their entirety. Various modifications and variations of the described compositions and methods of the invention will be apparent to those skilled in the art without departing from the scope and spirit of the invention. Although the invention has been described in connection with specific embodiments, it will be understood that the invention should not be unduly limited to such specific embodiments. Indeed, various modifications of the described modes for carrying out the invention that are obvious to those skilled in the fields of molecular biology, medicine, immunology, pharmacology, virology, or related fields are intended to be within the scope of the invention.

What is claimed is:

1. A method comprising:

testing and confirming that an individual is infected with or has been exposed to a filovirus; and administering an effective amount of clarithromycin and an effective amount of rifabutin to the individual, wherein administration of the effective amount of clarithromycin and the effective amount of rifabutin results in an inhibition in viral replication or a decrease in viral load, and wherein the step of administering is carried out for a suitable time period so that the individual is treated.

2. The method of claim 1, further comprising measuring, at two or more different times during the suitable time period, the viral load using a nucleic acid amplification based test.

3. The method of claim 1, wherein the inhibition in viral replication or the decrease in viral load is at least 10% after administration for the suitable time period.

4. The method of claim 1, wherein the individual is a human.

5. The method of claim 1, wherein the filovirus is Ebola virus or Marburg virus.

6. The method of claim 1, wherein the filovirus is Ebola virus.

7. The method of claim 1, further comprising measuring the reduction of at least one symptom resulting from the filovirus.

8. The method of claim 1 wherein administration of the effective amount of clarithromycin and the effective amount of rifabutin results in a synergistic inhibition in viral replication or a synergistic decrease in viral load.

* * * * *